US009642695B2

(12) United States Patent
Yamaoka et al.

(10) Patent No.: US 9,642,695 B2
(45) Date of Patent: May 9, 2017

(54) ARTIFICIAL BLOOD VESSEL, AND METHOD FOR PRODUCING ARTIFICIAL BLOOD VESSEL

(71) Applicants: JMS CO., Ltd., Hiroshima-shi, Hiroshima (JP); Tetsuji Yamaoka, Osaka (JP)

(72) Inventors: Tetsuji Yamaoka, Osaka (JP); Atsushi Mahara, Osaka (JP)

(73) Assignee: JMS CO., LTD., Osaka (JP)

( * ) Notice: Subject to any disclaimer, the term of this patent is extended or adjusted under 35 U.S.C. 154(b) by 0 days.

(21) Appl. No.: 14/438,531

(22) PCT Filed: Sep. 5, 2013

(86) PCT No.: PCT/JP2013/073891
§ 371 (c)(1),
(2) Date: Apr. 24, 2015

(87) PCT Pub. No.: WO2014/065017
PCT Pub. Date: May 1, 2014

(65) Prior Publication Data
US 2015/0272719 A1 Oct. 1, 2015

(30) Foreign Application Priority Data

Oct. 26, 2012 (JP) ................................. 2012-237258

(51) Int. Cl.
A61F 2/06 (2013.01)
A61K 35/12 (2015.01)
(Continued)

(52) U.S. Cl.
CPC ............... A61F 2/062 (2013.01); A61F 2/82 (2013.01); A61K 35/12 (2013.01); A61L 27/36 (2013.01);
(Continued)

(58) Field of Classification Search
CPC ........ A61F 2/062; A61F 2/82; A61F 2210/00; A61F 2240/00; A61F 2250/0058
See application file for complete search history.

(56) References Cited

U.S. PATENT DOCUMENTS 5,733,538 A * 3/1998 Riffle ................. A61L 33/0076
424/78.08
2002/0077697 A1 6/2002 Ranieri et al.
(Continued)

FOREIGN PATENT DOCUMENTS

JP 2010-504972 2/2010

OTHER PUBLICATIONS

International preliminary report on patentability of PCT/JP2013/073891 dated Apr. 28, 2015.
(Continued)

Primary Examiner — Paul Prebilic
(74) Attorney, Agent, or Firm — Kristina Castellano; Castellano PLLC

(57) ABSTRACT

In order to provide an artificial blood vessel that can prevent formation of a thrombus and a method for producing the artificial blood vessel, an artificial blood vessel is used (i) in which a peptide including a specific amino acid sequence has been added to an extracellular matrix obtained from a bio-derived vascular tissue and (ii) whose lumen has a cross sectional diameter of 4 mm or less.

15 Claims, 14 Drawing Sheets

(51) Int. Cl.
*C07K 14/78* (2006.01)
*A61L 27/36* (2006.01)
*A61L 27/50* (2006.01)
*A61F 2/82* (2013.01)
*A61K 35/44* (2015.01)

(52) U.S. Cl.
CPC ......... *A61L 27/3683* (2013.01); *A61L 27/507* (2013.01); *C07K 14/78* (2013.01); *A61F 2210/0076* (2013.01); *A61F 2240/001* (2013.01); *A61K 35/44* (2013.01)

(56) References Cited

U.S. PATENT DOCUMENTS

| 2006/0110720 | A1 | 5/2006 | Fujisato et al. | |
|---|---|---|---|---|
| 2009/0162437 | A1 | 6/2009 | Horii et al. | |
| 2009/0304772 | A1* | 12/2009 | Choubey | A61F 2/0077 424/423 |
| 2010/0125330 | A1* | 5/2010 | Belenkaya | A61L 27/18 623/1.46 |

OTHER PUBLICATIONS

International Search Report of PCT/JP2013/073891 dated Dec. 10, 2013.
Mahara, A., et al., Small-caliber longbypass graft by using decellularized ostrich carotid artery and peptide modification, Polymer Preprints, Japan, May 14, 2013, vol. 62, No. 1, p. 1773.
Tetsuji Yamaoka et al., "Acellular vascular grafts for regenerative medicine", Recent Advances in Cardiovascular Disease, Nov. 30, 2012 (Nov. 30, 2012), vol. 33, No. 1, pp. 56 to 63.
Mahara, A., et al., Small-caliber decellularized long-bypass graft by using peptide modification, Polymer Preprints, Japan, May 9, 2012, vol. 61, No. 2, pp. 4761-4762.
Mahara, A., et al., Surface modification procedure of acellular vascular grafts with the cell binding peptide, Polymer Preprints, Japan, 2011, vol. 60, No. 1, p. 1751, dated May 10, 2011.
Haruka Yamaguchi et al., "Noninvasive Evaluation of Calcification in Acellular Blood Vessels" The 31st Annual Meeting of the Japanese Society for Biomaterials Compilation of abstracts of p. 374, dated Nov. 16, 2009.
Funamoto, S., et al., The use of high-hydrostatic pressure treatment to decellularize blood vessels, Biomaterials, 2010, vol. 31, No. 13, pp. 3590-3595, dated Feb. 9, 2010.
Sasaki, S., et al., In vivo evaluation of a novel scaffold for artificial corneas prepared by using ultrahigh hydrostatic pressure to decellularize porcine corneas, Molecular Vision, 2009, vol. 15, pp. 2022-2028, dated Oct. 13, 2009.
Tetsuji Yamaoka et al., "Luminal surface modification and the patency of small-diameter acellular vascular grafts", ABML2011(Assistive Technology, Bio Medical Engineering and Life Support) Compilation of theses pp. OS2-4-1 and OS2-4-2, dated Nov. 3, 2011.
Atsushi Mahara et al., "Evaluation of patency of acellular small diameter vascular graft which is surface modified by endothelial cell adhesive peptide", Regenerative Medicine, Extra issue The Japanese Society for Regenerative Medicine magazine vol. 11, Suppl. 2012 Program/Abstract of the 11th Congress of Japanese Society for Regenerative Medicine p. 174, O-10-5, dated May 16, 2012.

* cited by examiner (a)

(b)

(a)

(b)

```
                       SEQUENCE LISTING

<160> NUMBER OF SEQ ID NOS: 10

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Arg Glu Asp Val
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 2

Gly Gly Gly Gly
1

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

Gly Gly Gly Gly Gly
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 4

Ala Ala Ala Ala
```

-continued

```
<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 5

Ala Ala Ala Ala Ala
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa is Hydroxyproline
<220> FEATURE:
<221> NAME/KEY: misc_feature
<222> LOCATION: (5)..(5)
<223> OTHER INFORMATION: Xaa is Hydroxyproline
<220> FEATURE:
<221> NAME/KEY: misc_feature
<222> LOCATION: (8)..(8)
<223> OTHER INFORMATION: Xaa is Hydroxyproline

<400> SEQUENCE: 6

Pro Xaa Gly Pro Xaa Gly Pro Xaa Gly Gly Gly Gly
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa is Hydroxyproline
<220> FEATURE:
<221> NAME/KEY: misc_feature
<222> LOCATION: (5)..(5)
<223> OTHER INFORMATION: Xaa is Hydroxyproline
<220> FEATURE:
<221> NAME/KEY: misc_feature
<222> LOCATION: (8)..(8)
<223> OTHER INFORMATION: Xaa is Hydroxyproline

<400> SEQUENCE: 7

Pro Xaa Gly Pro Xaa Gly Pro Xaa Gly Gly Gly Gly Arg Glu Asp Val
1               5                   10                  15

<210> SEQ ID NO 8
<211> LENGTH: 24
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa is Hydroxyproline
<220> FEATURE:
<221> NAME/KEY: misc_feature
<222> LOCATION: (5)..(5)
```

```
<223> OTHER INFORMATION: Xaa is Hydroxyproline
<220> FEATURE:
<221> NAME/KEY: misc_feature
<222> LOCATION: (8)..(8)
<223> OTHER INFORMATION: Xaa is Hydroxyproline
<220> FEATURE:
<221> NAME/KEY: misc_feature
<222> LOCATION: (11)..(11)
<223> OTHER INFORMATION: Xaa is Hydroxyproline
<220> FEATURE:
<221> NAME/KEY: misc_feature
<222> LOCATION: (14)..(14)
<223> OTHER INFORMATION: Xaa is Hydroxyproline
<220> FEATURE:
<221> NAME/KEY: misc_feature
<222> LOCATION: (17)..(17)
<223> OTHER INFORMATION: Xaa is Hydroxyproline
<220> FEATURE:
<221> NAME/KEY: misc_feature
<222> LOCATION: (20)..(20)
<223> OTHER INFORMATION: Xaa is Hydroxyproline

<400> SEQUENCE: 8

Pro Xaa Gly Pro Xaa Gly Pro Xaa Gly Pro Xaa Gly Pro Xaa Gly Pro
1               5                   10                  15

Xaa Gly Pro Xaa Gly Gly Gly Gly
            20

<210> SEQ ID NO 9
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa is Hydroxyproline
<220> FEATURE:
<221> NAME/KEY: misc_feature
<222> LOCATION: (5)..(5)
<223> OTHER INFORMATION: Xaa is Hydroxyproline
<220> FEATURE:
<221> NAME/KEY: misc_feature
<222> LOCATION: (8)..(8)
<223> OTHER INFORMATION: Xaa is Hydroxyproline
<220> FEATURE:
<221> NAME/KEY: misc_feature
<222> LOCATION: (11)..(11)
<223> OTHER INFORMATION: Xaa is Hydroxyproline
<220> FEATURE:
<221> NAME/KEY: misc_feature
<222> LOCATION: (14)..(14)
<223> OTHER INFORMATION: Xaa is Hydroxyproline
<220> FEATURE:
<221> NAME/KEY: misc_feature
<222> LOCATION: (17)..(17)
<223> OTHER INFORMATION: Xaa is Hydroxyproline
<220> FEATURE:
<221> NAME/KEY: misc_feature
<222> LOCATION: (20)..(20)
<223> OTHER INFORMATION: Xaa is Hydroxyproline

<400> SEQUENCE: 9

Pro Xaa Gly Pro Xaa Gly Pro Xaa Gly Pro Xaa Gly Pro Xaa Gly Pro
1               5                   10                  15

Xaa Gly Pro Xaa Gly Gly Gly Gly Arg Glu Asp Val
            20                  25

<210> SEQ ID NO 10
<211> LENGTH: 28
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is Hydroxyproline
<220> FEATURE:
<221> NAME/KEY: misc_feature
<222> LOCATION: (4)..(4)
<223> OTHER INFORMATION: Xaa is Hydroxyproline
<220> FEATURE:
<221> NAME/KEY: misc_feature
<222> LOCATION: (7)..(7)
<223> OTHER INFORMATION: Xaa is Hydroxyproline
<220> FEATURE:
<221> NAME/KEY: misc_feature
<222> LOCATION: (10)..(10)
<223> OTHER INFORMATION: Xaa is Hydroxyproline
<220> FEATURE:
<221> NAME/KEY: misc_feature
<222> LOCATION: (13)..(13)
<223> OTHER INFORMATION: Xaa is Hydroxyproline
<220> FEATURE:
<221> NAME/KEY: misc_feature
<222> LOCATION: (16)..(16)
<223> OTHER INFORMATION: Xaa is Hydroxyproline
<220> FEATURE:
<221> NAME/KEY: misc_feature
<222> LOCATION: (19)..(19)
<223> OTHER INFORMATION: Xaa is Hydroxyproline

<400> SEQUENCE: 10

Xaa Pro Gly Xaa Pro Gly Xaa Pro Gly Xaa Pro Gly Xaa Pro Gly Xaa
1               5                   10                  15

Pro Gly Xaa Pro Gly Gly Gly Gly Arg Glu Asp Val
            20                  25
```

ARTIFICIAL BLOOD VESSEL, AND METHOD FOR PRODUCING ARTIFICIAL BLOOD VESSEL

CROSS REFERENCE TO RELATED APPLICATIONS

This application is a U.S. National Stage Application of PCT/JP2013/073891 filed on Sep. 5, 2013, which claims priority to Japanese patent application 2012-237258, filed on Oct. 26, 2012, both of which are incorporated herein by reference in their entireties.

TECHNICAL FIELD

The present invention relates to an artificial blood vessel and a method for producing an artificial blood vessel.

BACKGROUND ART

Recently, attention is being given to an artificial tissue which can function in a living body instead of an original tissue of the living body, and development of such an artificial tissue is proceeding.

For example, Patent Literatures 1 and 2 disclose techniques in which a connective tissue is extracted by removing cells and the like from various kinds of tissues derived from an animal that can be transplanted, and the connective tissue thus extracted is used as an artificial tissue.

A variety of the artificial tissue is wide and, for example, development of artificial tissues is proceeding which can serve as soft tissues (e.g., a blood vessel, a heart valve, a cornea, an amnion, a dura mater, and the like), hard tissues (e.g., a bone, a cartilage, a tooth, and the like), or organs (e.g., a heart, a kidney, a liver, a pancreas, a brain, and the like).

Among tissues that exist in a living body, a blood vessel is a tissue which includes a large number of variations in terms of thickness, length, bifurcation, and the like. Moreover, the blood vessel needs to have high strength because (i) the blood vessel is exposed to a severe environment, i.e., is constantly subjected to pressure by a blood flow and (ii) large force is applied to the blood vessel in surgery such as suture.

In recent years, as the number of patients suffering from circulatory system diseases increases, demands for artificial blood vessels increase. In order to meet such demands, various artificial blood vessels have been developed and used.

For example, artificial blood vessels made of synthetic polymers such as ePTFE and Dacron (Registered Trademark) have been developed and used. The artificial blood vessels made of such synthetic polymers effectively function in a case where a cross section of its lumen is large (in other words, in a case of having a medium diameter or a large diameter), and approximately 700,000 pieces of such artificial blood vessels are used per year.

CITATION LIST

Patent Literature

[Patent Literature 1]
Japanese Patent Application Publication Tokukai No. 2004-97552 (Publication date: Apr. 2, 2004)
[Patent Literature 2]
US2002/0077697A1 (Publication date: Jun. 20, 2002)

SUMMARY OF INVENTION

Technical Problem

However, the conventional artificial blood vessel as above described has a problem that, in a case where a lumen of the artificial blood vessel is thin, a thrombus easily occurs in the lumen.

For example, in a case where an artificial blood vessel has a lumen whose cross sectional shape is a circular shape and a diameter of the circle is 4 mm or less, a thrombus is formed in the lumen of the artificial blood vessel in a short time from when the artificial blood vessel has been transplanted, and a blood flow is inhibited by the thrombus.

The present invention is accomplished in view of the conventional problems, and its object is to provide (i) an artificial blood vessel that can prevent formation of a thrombus and (ii) a method for producing the artificial blood vessel.

Solution to Problem

In order to attain the object, the artificial blood vessel of the present invention is an artificial blood vessel formed from an extracellular matrix obtained by removing cells from a bio-derived vascular tissue, in which: a cross sectional diameter of a lumen of the artificial blood vessel is 4 mm or less; and a peptide has been added to the extracellular matrix, the peptide including an amino acid sequence $(POG)_n$-X-$(REDV)_m$ (where each of n and m is an arbitrary integer of 1 or more, and X is a peptide linker made up of an amino acid(s) whose number is 0 or more).

In order to attain the object, the method for producing the artificial blood vessel of the present invention includes the steps of: (1) obtaining an extracellular matrix by removing cells from a bio-derived vascular tissue whose lumen has a cross sectional diameter of 4 mm or less; and (2) adding, to the extracellular matrix, a peptide that includes an amino acid sequence $(POG)_n$-X-$(REDV)_m$ (where each of n and m is an arbitrary integer of 1 or more, and X is a peptide linker made up of an amino acid(s) whose number is 0 or more).

Advantageous Effects of Invention

The present invention brings about an effect of preventing a thrombus from being formed in a lumen of an artificial blood vessel even in a case where the lumen of the artificial blood vessel is thin.

According to the present invention, the artificial blood vessel is produced by the use of the extracellular matrix derived from a living body. This brings about an effect of providing an artificial blood vessel that is highly adaptable to a living body.

According to the present invention, the cells and the cellular constituents (e.g., DNA and the like) which are derived from the living body have been efficiently removed from the extracellular matrix, and it is therefore possible to prevent rejection that may occur when the artificial blood vessel is transplanted. Specifically, rejection occurs in a case where (i) cells and cellular constituents remain in an extracellular matrix and (ii) an artificial blood vessel produced from such an extracellular matrix is transplanted into a species (e.g., a human, a pig) that is different from a species (e.g., an ostrich) from which the extracellular matrix has been derived. However, according to the present invention, cells and cellular constituents derived from a living body have been efficiently removed from an extracellular matrix, and it is therefore possible to prevent occurrence of such rejection.

The present invention brings about an effect of providing an artificial blood vessel which (i) has a thin lumen (e.g., in a case where a cross sectional shape of the lumen is a circular shape, a diameter of the circle is 4 mm or less), (ii) is long (e.g., 40 cm or more), and (iii) hardly has a bifurcation (e.g., no bifurcation). Such an artificial blood vessel can be widely used in a clinical practice. For example, in a clinical practice, it is sometimes necessary to form a bypass between blood vessels that are distant from each other. According to the artificial blood vessel of the present invention, it is possible to easily form such a bypass.

The present invention brings about an effect of providing an artificial blood vessel that is highly strong. That is, the present invention brings about an effect of providing an artificial blood vessel that will not be broken by suture in surgery, in other words, that makes the surgery easy. Moreover, the present invention brings about an effect of providing an artificial blood vessel that is highly strong and can therefore be used of course as a blood vessel for a vein and also as a blood vessel for an artery.

The present invention brings about an effect of providing an artificial blood vessel that can stably function for a long time in a living body into which the artificial blood vessel has been transplanted.

DESCRIPTION OF EMBODIMENTS

Figure 1:
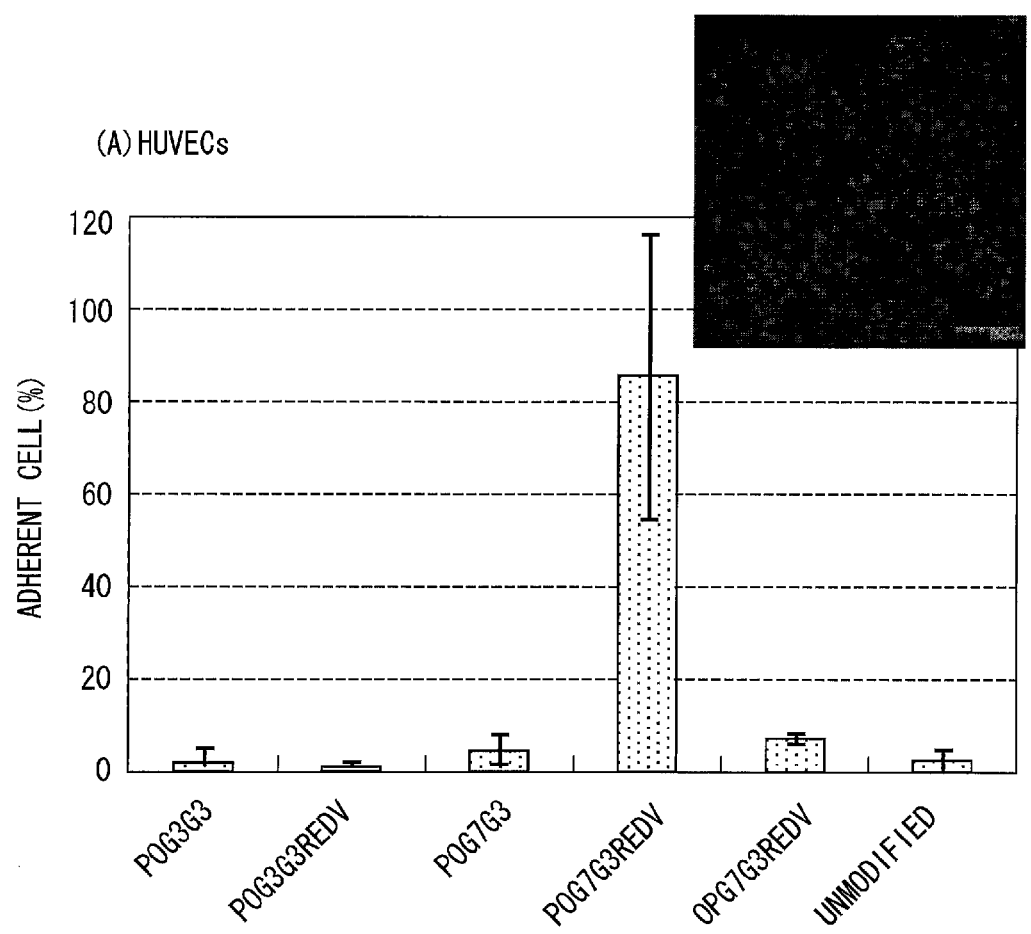
FIG. 1 is a graph illustrating cell adhesion activities of respective peptides in Example of the present invention.

The following description will discuss an embodiment of the present invention. Note, however, that the present invention is not limited to this.

[1. Artificial Blood Vessel]

An artificial blood vessel of the present embodiment is formed from an extracellular matrix which has been obtained by removing cells from a bio-derived vascular tissue by, for example, applying pressure. Note that a method for removing cells is not limited to this method. This point will be described later.

The extracellular matrix which has been obtained by applying pressure to a vascular tissue is (i) an extracellular matrix that is extremely close to an intact state and (ii) an extracellular matrix from which cells and cellular constituents have been efficiently removed. An artificial blood vessel which has been produced by the use of such an extracellular matrix can basically be an artificial blood vessel that is highly adaptable to a living body and hardly shows rejection.

The living body is not limited to a particular one and can be, for example, a non-human animal (e.g., a ratite, a bird, a mammal, or the like).

The mammal is not limited to a particular one and can be, for example, a mouse, a rat, a rabbit, a goat, a sheep, a monkey, or the like.

Among the living bodies, a ratite (e.g., an emu, a kiwi, an ostrich, a cassowary, a rhea, or the like) is preferable. In general, a ratite has a long neck, and blood vessels such as a carotid artery existing in the neck are thin and long and hardly have a bifurcation. From this, by producing an artificial blood vessel with the use of a blood vessel of a ratite, it is possible to provide an artificial blood vessel (i) whose lumen has a smaller cross section and (ii) which is longer and has less bifurcations. Such an artificial blood vessel is extremely useful in a clinical practice. Moreover, a ratite and the like are easy to raise, and it is therefore possible to stably supply a large number of vascular tissues.

The artificial blood vessel of the present embodiment is formed from an extracellular matrix which has been obtained by removing cells from a vascular tissue derived from the above described living body. Note that, in this specification, the term "vascular tissue" indicates a tissue that is made up of (i) an extracellular matrix constituting a blood vessel and (ii) cells constituting the blood vessel. Specifically, in this specification, the "vascular tissue" indicates a tissue that is made up of (i) an intima formed from endothelial cells and the like, (ii) a media formed from smooth muscle cells, elastic fibers, collagen fibers, and the like, and (iii) an adventitia formed from fibroblasts, a connective tissue, and the like.

A concrete configuration of the bio-derived vascular tissue is not limited to a particular one and can be an artery or a vein. The artificial blood vessel of the present embodiment is formed from the extracellular matrix that is extremely close to an intact state, and it is therefore possible to provide the artificial blood vessel that is extremely strong, regardless of whether an artery or a vein is used as a material. In view of providing an artificial blood vessel having greater strength, the vascular tissue is preferably an artery. Meanwhile, in view of providing an artificial blood vessel whose lumen has a larger capacity, the vascular tissue is preferably a vein. Therefore, a type of the vascular tissue may be selected as appropriate in accordance with a purpose of the artificial blood vessel.

The artificial blood vessel of the present embodiment can be used as an artificial blood vessel for an artery, or an artificial blood vessel for a vein. In a case where the artificial blood vessel of the present invention is used as a blood vessel (specifically, as an artificial blood vessel for an artery) in a part at which blood flows faster, the artificial blood vessel tends to prevent a thrombus more effectively. In such a part at which blood flows fast, higher pressure is applied to the artificial blood vessel, and it is therefore preferable that the artificial blood vessel has greater strength. From this, in a case where an artificial blood vessel for an artery is produced, the vascular tissue is preferably an artery.

Moreover, the artificial blood vessel of the present embodiment contains an extremely small amount of cells and cellular constituents which are derived from the living body from which the extracellular matrix is obtained. It is therefore possible to prevent occurrence of rejection with respect to the artificial blood vessel. From this, the artificial blood vessel of the present embodiment can be an artificial blood vessel to be transplanted into a living body (e.g., a mammal) whose species is different from the living body (e.g., a ratite) from which the extracellular matrix has been obtained. Of course, the artificial blood vessel of the present embodiment can be an artificial blood vessel to be transplanted into a living body whose species is identical with that of the living body from which the extracellular matrix has been obtained.

According to the present invention, the cells and the cellular constituents (e.g., DNA and the like) which are derived from the living body have been efficiently removed from the extracellular matrix, and it is therefore possible to prevent rejection that may occur when the artificial blood vessel is transplanted. Specifically, rejection occurs in a case where (i) cells and cellular constituents remain in an extracellular matrix and (ii) an artificial blood vessel produced from such an extracellular matrix is transplanted into a species (e.g., a human, a pig) that is different from a species (e.g., an ostrich) from which the extracellular matrix has been derived. However, according to the present invention, cells and cellular constituents derived from a living body have been efficiently removed from an extracellular matrix, and it is therefore possible to prevent occurrence of such rejection.

As above described, the artificial blood vessel of the present embodiment is formed from the extracellular matrix that has been obtained by carrying out a treatment such as applying pressure to a vascular tissue.

Details of the treatment will be described in [2-1. Step (1)] below, and are therefore not described here.

Constituents of the artificial blood vessel of the present embodiment are not limited, and the artificial blood vessel of the present embodiment can be formed from, for example, at least a von Willebrand factor, Vimentin, α Smooth muscle actin, and a substance stained by an Elastica van Gieson stain.

More specifically, the artificial blood vessel of the present embodiment can be formed from at least a von Willebrand factor, Vimentin, α Smooth muscle actin, a substance stained by an Elastica van Gieson stain, collagen, and elastin.

According to the configuration, the artificial blood vessel of the present embodiment contains the extracellular matrix that is extremely close to an intact state, and it is therefore possible to provide an artificial blood vessel that functions better.

Assuming that the artificial blood vessel of the present embodiment has a lumen whose cross sectional shape is a circular shape, a diameter of the circle can be 4 mm or less, 3 mm or less, 2 mm or less, 1.5 mm or less, or 1 mm or less. Note that, by appropriately selecting a vascular tissue as a material, it is possible to provide the artificial blood vessel whose lumen has an intended thickness.

The artificial blood vessel of the present embodiment can effectively prevent formation of a thrombus, and it is therefore possible to prevent a thrombus from being formed in a lumen even in a case where, of course, the lumen of the artificial blood vessel has a large circular shape and also in a case where the lumen of the artificial blood vessel has a small circular shape (e.g., a diameter of the circle is 4 mm or less).

Moreover, according to the artificial blood vessel of the present embodiment, a cross sectional area of the lumen can be $\pi \times 2^2$ mm$^2$ or less, $\pi \times 1.5^2$ mm$^2$ or less, $\pi \times 1^2$ mm$^2$ or less, $\pi \times 0.75^2$ mm$^2$ or less, or $\pi \times 0.5^2$ mm$^2$ (where $\pi \approx 3.14$). Note that, in this case, the cross sectional shape of the lumen of the artificial blood vessel is not necessarily a perfect circle.

The artificial blood vessel of the present embodiment can effectively prevent formation of a thrombus, and it is therefore possible to prevent a thrombus from being formed in the lumen even in a case where, of course, a cross sectional area of the lumen of the artificial blood vessel is large and also in a case where the cross sectional area of the lumen of the artificial blood vessel is small (e.g., the cross sectional area of the lumen is $\pi \times 2^2$ mm$^2$ or less).

A length of the artificial blood vessel of the present embodiment is not limited to a particular one and can be, for example, 10 cm or more, 20 cm or more, 30 cm or more, 40 cm or more, 50 cm or more, 60 cm or more, 70 cm or more, or 80 cm or more. The length of the artificial blood vessel is preferably 40 cm or more, more preferably 80 cm or more.

According to the configuration, it is possible to provide an artificial blood vessel that has a length sufficiently utilizable even in a clinical practice. For example, in a clinical practice, it is sometimes necessary to form a bypass between blood vessels that are distant from each other. According to the configuration of the present embodiment, it is possible to easily form such a bypass.

According to the artificial blood vessel of the present embodiment, a peptide, which includes an amino acid sequence (POG)$_n$-X-(REDV)$_m$ (where each of n and m is an arbitrary integer of 1 or more, and X is a peptide linker made up of an amino acid(s) whose number is 0 or more), can be added to the extracellular matrix. Note that, in the amino acid sequence, "O" represents hydroxyproline.

The "POG" in the amino acid sequence is an amino acid sequence that may bind to collagen contained in the extracellular matrix, and the "REDV" (SEQ ID NO: 1) in the amino acid sequence is an amino acid sequence that may bind to cells (e.g., cells that constitute a blood vessel) after the artificial blood vessel has been transplanted into the living body.

In a case where the peptide is added to the extracellular matrix, the peptide can be bonded to the extracellular matrix via a chemical bond (e.g., covalent bond or the like), or the peptide can be adsorbed onto the extracellular matrix via a chemical bond (e.g., hydrophobic bond or hydrogen bond). That is, an interaction form between the extracellular matrix and the peptide is not limited to a particular one.

The peptide can be a peptide that is made up of an amino acid sequence $(POG)_n$-X-$(REDV)_m$ or can be a peptide in which another amino acid sequence is bonded to the peptide that is made up of the amino acid sequence $(POG)_n$-X-$(REDV)_m$.

In a case where the another amino acid sequence is bonded, the another amino acid sequence can be bonded to at least one of a C-terminus and an N-terminus of the peptide made up of the amino acid sequence $(POG)_n$-X-$(REDV)_m$.

A concrete example of the another amino acid sequence to be bonded is not limited to a particular one and, for example, a peptide made up of an amino acid sequence $(POG)_n$-X-$(REDV)_m$ can be bonded to at least one of a C-terminus and an N-terminus of a peptide made up of an amino acid sequence $(POG)_n$-X-$(REDV)_m$ in a tandem manner. Note that, in this case, the amino acid sequences $(POG)_n$-X-$(REDV)_m$ can be identical ones or can be different ones. According to the configuration, it is possible to more effectively prevent a thrombus from being formed in the lumen of the artificial blood vessel.

Alternatively, a concrete example of the another amino acid sequence to be bonded can be, for example, a tag (e.g., Myc tag, His tag, HA tag, GST protein, or the like). According to the configuration, it is possible to easily purify the peptide made up of an amino acid sequence $(POG)_n$-X-$(REDV)_m$ with high purity.

Alternatively, a concrete example of the another amino acid sequence to be bonded can be, for example, an RGDS sequence or a GVPGI sequence. According to the configuration, it is possible to facilitate cell adhesion and/or to facilitate adhesion and proliferation of endothelial cells.

In the amino acid sequence above described, n and m can independently be an arbitrary integer of 1 or more.

For example, n is not limited to a particular one provided that n is an integer of 1 or more, and can be, for example, an integer of 1 or more and 20 or less, an integer of 2 or more and 20 or less, an integer of 3 or more and 20 or less, an integer of 4 or more and 20 or less, an integer of 5 or more and 20 or less, an integer of 6 or more and 20 or less, an integer of 7 or more and 20 or less, an integer of 8 or more and 20 or less, an integer of 9 or more and 20 or less, or an integer of 10 or more and 20 or less. Note that, although an upper limit of n is 20 in the above examples, the upper limit is not limited to this. For example, in each of the cases, the upper limit of n can be 30, 40, 50, or a larger value.

Meanwhile, m is not limited to a particular one provided that m is an integer of 1 or more, and can be, for example, an integer of 1 or more and 50 or less, an integer of 1 or more and 40 or less, an integer of 1 or more and 30 or less, an integer of 1 or more and 20 or less, an integer of 1 or more and 15 or less, an integer of 1 or more and 10 or less, or an integer of 1 or more and 5 or less. Of course, an upper limit of m can be larger than 50.

A combination of n and m can be any of combinations of all the values above described. For example, it is possible that n is an "integer of 3 or more and 20 or less" and m is an "integer of 1 or more and 10 or less", or it is possible that n is an "integer of 7 or more and 20 or less" and m is an "integer of 1 or more and 10 or less". According to the configuration, it is possible to further prevent formation of a thrombus.

In the amino acid sequence, "X" is a peptide linker for connecting "POG" with "REDV". According to the artificial blood vessel of the present embodiment, "POG" and "REDV" can be directly connected to each other. In such a case, "X" is to be omitted.

A concrete configuration of the X is not limited to a particular one. Note, however, that the configuration of the X is preferably one (i) that does not impair functions of "POG" and "REDV" and (ii) that can effectively present "POG" and "REDV" to collagen and a cell to which "POG" and "REDV" are connected, respectively.

A concrete configuration of the X is preferably, for example, a peptide linker made up of G (glycine) whose number is 1 or more, a peptide linker made up of A (alanine) whose number is 1 or more, a peptide linker made up of S (serine) whose number is 1 or more, or a peptide linker made up of at least two amino acids selected from the group consisting of G (glycine), A (alanine), and S (serine).

The concrete configuration of the X is further preferably (i) a peptide linker made up of G (glycine) whose number is 1 or more or (ii) a peptide linker made up of A (alanine) whose number is 1 or more.

Each of G (glycine) and A (alanine) is an amino acid that has a small aliphatic side chain. These amino acids have the small side chain (i.e., a steric hindrance is small), and it is therefore possible to effectively present "POG" and "REDV" to respective connection targets. For example, these amino acids do not prevent "POG" and "REDV" from approaching and connecting to the respective connection targets. Moreover, these amino acids have the small aliphatic side chain, and it is therefore possible to inhibit influence to functions of "POG" and "REDV". For example, in these amino acids, a large polarity does not exist at the side chain, and therefore steric structures of "POG" and "REDV" will not be largely changed.

In a case where the "X" is made up of a plurality of amino acids, the number of amino acids constituting the "X" is not limited to a particular one, and the number of amino acids can be, for example, 1, 2, 3, 4, or 5. Of course, the number of amino acids can be 6 or more. For example, the X can be "G", "GG", "GGG", "GGGG" (SEQ ID NO 2), "GGGGG" (SEQ ID NO: 3), "A", "AA", "AAA", "AAAA" (SEQ ID NO: 4), or "AAAAA" (SEQ ID NO: 5). Of course, the X is not limited to these.

In a case where the "X", which is a peptide linker made up of an amino acid, is omitted, it is possible to directly connect "POG" with "REDV" and, alternatively, "POG" and "REDV" can be connected with each other via a linker other than an amino acid.

Such a linker is not limited to a particular one and can be, for example, sugar, fat, a nucleic acid, or a synthetic polymer. In a case where "X" in the peptide made up of the amino acid sequence $(POG)_n$-X-$(REDV)_m$ is a peptide linker made up of an amino acid whose number is 0, it is possible that (i) "POG" and "REDV" are directly connected with each other or (ii) "POG" and "REDV" are connected with each other via a linker other than an amino acid.

According to the artificial blood vessel of the present embodiment, the above described extracellular matrix has been preferably subjected to a DNase treatment.

According to the configuration, it is possible to more efficiently destroy and remove cells and cellular constituents (specifically, DNA) which remain in the extracellular matrix. As a removal ratio of cells and cellular constituents from the extracellular matrix increases higher, it is possible to further prevent various problems (e.g., rejection and the like) which may occur when the artificial blood vessel is transplanted.

Note that details of the DNase treatment will be described later in [2-3. Step (3)], and are therefore not described here.

According to the artificial blood vessel of the present embodiment, the extracellular matrix has preferably been washed with a cleaning liquid.

According to the configuration, it is possible to more efficiently remove cells and cellular constituents (specifically, DNA) which remain in the extracellular matrix. As a removal ratio of cells and cellular constituents from the extracellular matrix increases higher, it is possible to further prevent various problems (e.g., rejection and the like) which may occur when the artificial blood vessel is transplanted.

Note that details of the washing treatment will be described later in [2-4. Step (4)], and are therefore not described here.

The artificial blood vessel of the present invention can be configured as follows:

According to the artificial blood vessel of the present invention, it is preferable that the n is an integer of 3 or more and 20 or less; and the m is an integer of 1 or more and 10 or less.

According to the artificial blood vessel of the present invention, it is preferable that the X is a peptide linker made up of glycine whose number is 1 or more, a peptide linker made up of alanine whose number is 1 or more, a peptide linker made up of serine whose number is 1 or more, or a peptide linker made up of at least two amino acids selected from the group consisting of glycine, alanine, and serine.

According to the artificial blood vessel of the present invention, it is preferable that the extracellular matrix is obtained by removing cells by applying pressure to the bio-derived vascular tissue.

According to the artificial blood vessel of the present invention, it is preferable that the extracellular matrix has been subjected to a DNase treatment.

According to the artificial blood vessel of the present invention, it is preferable that the extracellular matrix has been washed with a cleaning liquid for a time period of three days or shorter.

According to the artificial blood vessel of the present invention, it is preferable that the extracellular matrix contains a von Willebrand factor, Vimentin, α Smooth muscle actin, a substance stained by an Elastica van Gieson stain, collagen, and elastin which are maintained in an intact state.

According to the artificial blood vessel of the present invention, it is preferable that the bio-derived vascular tissue is derived from a ratite, a bird, or a mammal.

According to the artificial blood vessel of the present invention, it is preferable that the artificial blood vessel is transplanted into a living body whose species is different from that of a living body from which the bio-derived vascular tissue is derived.

[2. Method for Producing Artificial Blood Vessel]

A method for producing the artificial blood vessel of the present embodiment includes the steps (1) and (2).

Moreover, in addition to the steps (1) and (2), the method for producing the artificial blood vessel of the present embodiment can include the steps (3) and (4), and the like.

The following description will discuss the steps.

[2-1. Step (1)]

The method of the present embodiment for producing an artificial blood vessel includes the step (1) of obtaining an extracellular matrix by removing cells from a bio-derived vascular tissue.

A concrete method of the step (1) is not limited to a particular one and can be, for example, (i) the step of obtaining an extracellular matrix by removing cells from a bio-derived vascular tissue by applying pressure to the bio-derived vascular tissue, (ii) the step of obtaining an extracellular matrix by removing cells from a bio-derived vascular tissue by treating the bio-derived vascular tissue with use of a surfactant (e.g., dodecyl sodium sulfate, Triton X-100 (Registered Trademark), or sorbitan), or (iii) the step of treating a bio-derived vascular tissue with use of a solvent having a high salt concentration.

The extracellular matrix which has been obtained by applying pressure to a vascular tissue is (i) an extracellular matrix that is extremely close to an intact state and (ii) an extracellular matrix from which cells and cellular constituents have been efficiently removed. An artificial blood vessel which has been produced by the use of such an extracellular matrix can basically be an artificial blood vessel that is highly adaptable to a living body and shows less rejection.

The living body is not limited to a particular one and can be, for example, a non-human animal (e.g., a ratite, a bird, a mammal or the like). Further, the mammal is not limited to a particular one and can be, for example, a mouse, a rat, a rabbit, a goat, a sheep, a monkey, or the like.

Among the living bodies, a ratite (e.g., an emu, a kiwi, an ostrich, a cassowary, a rhea, or the like) is preferable. In general, a ratite has a long neck, and blood vessels such as a carotid artery existing in the neck are thin and long and hardly have a bifurcation. From this, by producing an artificial blood vessel with the use of a blood vessel of a ratite, it is possible to provide an artificial blood vessel (i) whose lumen is thin and (ii) which is longer and has less bifurcations. Such an artificial blood vessel is more useful in a clinical practice. Moreover, a ratite and the like are easy to raise, and it is therefore possible to stably supply a large number of vascular tissues.

A bio-derived vascular tissue is not limited to a particular one and can be an artery or a vein. In view of providing an artificial blood vessel having greater strength, the vascular tissue is preferably an artery. Meanwhile, in view of providing an artificial blood vessel whose lumen has a larger capacity, the vascular tissue is preferably a vein. Therefore, a type of the vascular tissue may be selected as appropriate in accordance with a purpose of the artificial blood vessel.

Assuming that the vascular tissue has a lumen whose cross sectional shape is a circular shape, a diameter of the circle is 4 mm or less. More specifically, the diameter of the circle can be 3 mm or less, 2 mm or less, 1.5 mm or less, or mm or less. Note that, by appropriately selecting a vascular tissue as a material, it is possible to provide the artificial blood vessel whose lumen has an intended thickness.

Moreover, according to the vascular tissue, a cross sectional area of the lumen can be $\pi \times 2^2$ mm$^2$ or less, $\pi \times 1.5^2$ mm$^2$ or less, $\pi \times 1^2$ mm$^2$ or less, $\pi \times 0.75^2$ mm$^2$ or less, or $\pi \times 0.5^2$ mm$^2$ or less (where $\pi \approx 3.14$). Note that, in this case, the cross sectional shape of the lumen of the vascular tissue is not necessarily a perfect circle.

A length of the vascular tissue is not limited to a particular one and can be, for example, 10 cm or more, 20 cm or more, 30 cm or more, 40 cm or more, 50 cm or more, 60 cm or more, 70 cm or more, or 80 cm or more. The length of the vascular tissue is preferably 40 cm or more, more preferably 80 cm or more.

According to the method of the present embodiment for producing an artificial blood vessel, in the step (1), the extracellular matrix is obtained by removing cells by applying pressure to the vascular tissue. In this case, an extracellular matrix in a substantially intact state is obtained. Therefore, a size of the artificial blood vessel becomes substantially the same as that of the original vascular tissue.

For example, in a case where the extracellular matrix is obtained by removing cells by applying pressure to the bio-derived vascular tissue and when pressure is reduced after pressure application to the vascular tissue, (i) the cells are ruptured and removed without use of a chemical substance etc. and (ii) a structure of the extracellular matrix is restored from a compressed state. This makes it possible to obtain an extracellular matrix in a more intact state.

The vascular tissue can be obtained by surgically harvesting a vascular tissue from a living body (e.g., non-human animal). Alternatively, the vascular tissue can be obtained by purchasing a commercially-available vascular tissue that has already been harvested.

In the above step (1), for example, the extracellular matrix is obtained by removing cells, for example, by applying pressure to the bio-derived vascular tissue. A concrete method of applying pressure is not limited to a particular one, and can be any method with which pressure is applied to the vascular tissue to an extent that cells and cell constituents are removed from the vascular tissue. Therefore, the step (1) can be carried out by use of a known pressure device as appropriate.

A magnitude of the pressure to be applied to the vascular tissue is not limited to a particular one, and is, for example, preferably 200 MPa or higher and 1000 MPa or lower, further preferably 300 MPa or higher and 1000 MPa or lower, and most preferably 500 MPa or higher and 1000 MPa or lower.

According to the configuration, it is possible (i) to more efficiently destroy cells contained in the vascular tissue and (ii) to more efficiently remove thus destroyed cells and cellular constituents from the extracellular matrix. As a removal ratio of cells and cellular constituents from the extracellular matrix increases higher, it is possible to further prevent various problems (e.g., rejection and the like) which may occur when the artificial blood vessel is transplanted.

A concrete method of applying pressure to the vascular tissue is not limited to a particular one. For example, the pressure can be applied to the vascular tissue in liquid.

The liquid is not limited to a particular one in concrete configuration, and can be, for example, PBS (phosphate buffered saline), physiological saline solution, or the like. In view of providing an artificial blood vessel having greater strength by obtaining an extracellular matrix in a more intact state, the above liquid is preferably physiological saline solution.

When the step (1) is carried out, temperature of the vascular tissue can be controlled at a specific temperature, but it is not necessary to control the temperature at a specific temperature. In a case where the temperature of the vascular tissue is controlled at a specific temperature, the temperature can be controlled at a temperature of, for example, 37° C. or higher and 100° C. or lower. According to the configuration, it is possible to obtain an extracellular matrix in a more intact state.

[2-2. Step (2)]

The method of the present embodiment for producing an artificial blood vessel includes the step (2) of adding, to the extracellular matrix, a peptide that includes an amino acid sequence $(POG)_n$-X-$(REDV)_m$ (where each of n and m is an arbitrary integer of 1 or more, and X is a peptide linker made up of an amino acid(s) whose number is 0 or more).

The details of a configuration of the peptide including the amino acid sequence $(POG)_n$-X-$(REDV)_m$ has been discussed above and therefore, an explanation thereof is omitted here.

In the step 2, in a case where the peptide is added to the extracellular matrix, the peptide can be bonded to the extracellular matrix via a chemical bond (e.g., covalent bond or the like), or the peptide can be adsorbed onto the extracellular matrix via a chemical bond (e.g., hydrophobic bond or hydrogen bond). That is, an interaction form between the extracellular matrix and the peptide is not limited to a particular one.

A concrete method of adding the peptide to the extracellular matrix is not limited to a particular one. For example, the peptide can be added to the extracellular matrix by mixing the extracellular matrix and the peptide. More specifically, the extracellular matrix can be added to the extracellular matrix by soaking the extracellular matrix in liquid containing the peptide.

The liquid containing the peptide is not limited to a particular one in concrete configuration, and can be, for example, PBS (phosphate buffered saline), physiological saline solution, or the like. In view of providing an artificial blood vessel having greater strength by obtaining an extracellular matrix in a more intact state, the liquid is preferably physiological saline solution.

In the step (2), the peptide can be added to the extracellular matrix while a mixture of the extracellular matrix and the peptide are being heated. A temperature for this heating is not limited to a particular one. The mixture is heated to, for example, preferably 37° C. or higher and 100° C. or lower, further preferably 60° C. or higher and 100° C. or lower, further preferably 60° C. or higher and 80° C. or lower, and most preferably 60° C. or higher and 75° C. or lower.

According to the configuration, it is possible (i) to efficiently add the peptide to the extracellular matrix and (ii) to efficiently destroy and remove cells and cellular constituents which remain in the extracellular matrix.

In the step (2), a heating time for the mixture of the extracellular matrix and the peptide is not limited to a particular one. The heating time can be, for example, preferably 1 minute or longer and 180 minutes or shorter, further preferably 10 minutes or longer and 120 minutes or shorter, and most preferably 30 minutes or longer and 60 minutes or shorter.

According to the configuration, the mixture is heated for a heating time that is neither too long nor too short. This makes it possible to more efficiently destroy and remove cells and cellular constituents which remain in the extracellular matrix.

In the step (2), a concentration of the peptide in the mixture of the extracellular matrix and the peptide is not limited to a particular one, but can be appropriately set. The concentration of the peptide in the mixture of the extracellular matrix and the peptide can be, for example, 1 μM or higher and 1 M or less, 10 μM or higher and 1 M or less, 100 μM or higher and 1 M or less, 1 mM or higher and 1 M or less, 10 mM or higher and 1 M or less, or 100 mM or higher or 1 M or less. Of course, the present invention is not limited to the above concentrations of the peptide.

According to the configuration, a large amount of peptide can be adhered to the extracellular matrix. This makes it possible to further prevent formation of a thrombus in the lumen of the artificial blood vessel.

In the step (2), in a case where the mixture of the extracellular matrix and the peptide is heated, it is possible to carry out a process for decreasing a temperature of the mixture after heating.

In such a case, a concrete method of decreasing the temperature is not specifically limited. For example, the temperature of the heated mixture can be gradually decreased by leaving the heated mixture at a room temperature (e.g., 25° C.). According to this configuration, because the temperature of the mixture gradually decreases, it is possible (i) to efficiently add the peptide to the extracellular matrix and (ii) to prevent denaturalization of the peptide which denaturalization may occur due to a sudden temperature change.

[2-3. Step (3)]

The method of the present embodiment for producing an artificial blood vessel can include the step (3) of carrying out a DNase treatment with respect to the extracellular matrix.

According to the configuration, it is possible to more efficiently destroy and remove cells and cellular constituents (specifically, DNA) which remain in the extracellular matrix. As a removal ratio of cells and cellular constituents from the extracellular matrix increases higher, it is possible to further prevent various problems (e.g., rejection and the like) which may occur when the artificial blood vessel is transplanted.

A time at which the step (3) is carried out is not limited to a particular one. For example, the step (3) can be carried out between the step (1) and the step (2) (e.g., in the order of the step (1)→the step (3)→the step (2)), or alternatively, after the step (1) and the step (2) (e.g., in the order of the step (1)→the step (2)→the step (3)). Of course, the present invention is not limited to the above described timings.

The DNase treatment in the step (3) can be carried out by adding DNase (e.g., any of various commercially available DNases) and the extracellular matrix into a liquid in which DNase can function.

The liquid is not limited to a particular one in concrete configuration, and can be, for example, a DNase treatment solution which is obtained by adding a bivalent ion source such as $MgCl_2$ and/or $CaCl_2$ to PBS (phosphate buffered saline), physiological saline solution, or the like. In view of providing an artificial blood vessel having greater strength by obtaining an extracellular matrix in a more intact state, the liquid is preferably physiological saline solution.

A concentration of DNase in the DNase treatment solution is not limited to a particular one, but can be, for example, 1 U/mL or higher and 1000 U/mL or lower, 10 U/mL or higher and 500 U/mL or lower, or 40 U/mL or higher and 100 U/mL or lower.

In the configuration, the DNase treatment is carried out with use of the DNase treatment solution having a DNase concentration that is neither too low nor too high. This makes it possible (i) to more efficiently destroy and remove cells and cellular constituents (specifically, DNA) which remain in the extracellular matrix and (ii) to suppress, to a low amount, an amount of DNase which remains in the artificial blood vessel. As a result, it becomes possible (i) to provide an artificial blood vessel having greater strength and (ii) to further prevent various problems (e.g., rejection etc.) that may occur when the artificial vessel is transplanted.

DNase requires bivalent ions (e.g., magnesium ions, calcium ions, and/or the like) for expression of activity. Therefore, preferably, the DNase treatment solution contains a bivalent ion source such as $MgCl_2$ and/or $CaCl_2$.

According to the configuration, it is possible to increase activity of DNase in the DNase treatment solution. Therefore, it is possible to more efficiently destroy and remove cells and cellular constituents (specifically, DNA) which remain in the extracellular matrix.

A concentration of $MgCl_2$ and $CaCl_2$ in the DNase treatment solution is not limited to a particular one, and can be appropriately set in accordance with a characteristic of DNase employed. The concentration of $MgCl_2$ and $CaCl_2$ in the DNase treatment solution can be, for example, 10 mM or higher and 50 mM or lower, 20 mM or higher and 40 mM or lower, or 20 mM. Of course, the present invention is not limited to those above described.

A temperature in the DNase treatment in the step (3) is not limited to a particular one, and can be appropriately set. The temperature can be, for example, 35° C. or higher and 40° C. or lower, or 37° C.

A treatment time of the DNase treatment in the step (3) is not limited to a particular one, but can be appropriately set. The treatment time is, for example, preferably 6 days or shorter, further preferably 5 days or shorter, further preferably 4 days or shorter, and most preferably 3 days or shorter. Note that a lower limit value of the treatment time is not limited to a particular one, and can be, for example, 0.5 day or 1 day.

According to the configuration, the artificial blood vessel is produced by use of an extracellular matrix in a more intact state. This makes it possible to provide an artificial blood vessel having greater strength.

The treatment time of the DNase treatment in the step (3) can also be appropriately set in accordance with a treatment time of the step (4) that will be discussed below. For example, preferably, a total time of the treatment time of the DNase treatment in the step (3) and the treatment time of the step (4) is 6 days or shorter.

According to the configuration, the artificial blood vessel is produced by use of an extracellular matrix in a more intact state. This makes it possible to provide an artificial blood vessel having greater strength.

In the above description, a concrete configuration of the step (3) is discussed. The step (3) is preferably a step that can more efficiently destroy and remove cells and cellular constituents (specifically, DNA) which remain in the extracellular matrix.

For example, on the premise that an amount of cells and cellular constituents which remain in the extracellular matrix obtained in the step (1) is 100 (100%), the step (3) is a step of reducing the amount to preferably 90 (90%) or less, further preferably 80 (80%) or less, further preferably 70 (70%) or less, further 60 (60%) or less, further preferably 50 (50%) or less, further preferably 40 (40%) or less, further preferably 30 (30%) or less, further preferably 20 (20%) or less, further preferably 10 (10%) or less, further preferably 5 (5%) or less, and further preferably 1 (1%) or less.

[2-4. Step (4)]

The method of the present embodiment for producing an artificial blood vessel can include the step (4) of subjecting the extracellular matrix to a washing treatment.

According to the configuration, it is possible to more efficiently remove cells and cellular constituents (specifically, DNA) which remain in the extracellular matrix. As a removal ratio of cells and cellular constituents from the extracellular matrix increases higher, it is possible to further prevent various problems (e.g., rejection and the like) which may occur when the artificial blood vessel is transplanted.

The washing treatment in the step (4) can be carried out by washing the extracellular matrix with a cleaning liquid. More specifically, the extracellular matrix can be washed by soaking the extracellular matrix in the cleaning liquid and in some cases, further shaking the extracellular matrix.

The cleaning liquid is not limited to a particular one in concrete configuration, and can be, for example, PBS (phosphate buffered saline), physiological saline solution, or the like. In view of providing an artificial blood vessel having greater strength by obtaining an extracellular matrix in a more intact state, the liquid is preferably physiological saline solution.

The above cleaning liquid preferably contains EDTA (ethylene diamine tetraacetic acid). According to the configuration, bivalent ions (e.g., magnesium ion etc.) can be chelated with EDTA. This makes it possible to inhibit activity of an enzyme(s) such as DNase (e.g., DNase originating from a vascular tissue and/or DNase employed in the step (3)). Such inhibition of activity of the enzyme such as DNase makes it possible to provide an artificial blood vessel having greater strength by obtaining an extracellular matrix in a more intact state.

A concentration of EDTA in the cleaning liquid is not limited to a particular one, and can be, for example, 1 mg/L or higher and 1 g/L or lower, 10 mg/L or higher and 1 g/L or lower, 100 mg/L or higher and 500 mg/L or lower, or 500 mg/L.

In the step (4), a washing treatment time is not limited to a particular one. The washing treatment time is, for example, preferably 6 days or shorter, further preferably 5 days or shorter, further preferably 4 days or shorter, and most preferably 3 days or shorter. Note that a lower limit value of this washing treatment time is not limited to a particular one, and can be, for example, 0.5 day or 1 day.

According to the configuration, it is possible to more efficiently destroy and remove cells and cellular constituents (specifically, DNA) which remain in the extracellular matrix. Therefore, it becomes possible to further prevent various problems (e.g., rejection and the like) which may occur when the artificial blood vessel is transplanted. Further, as shown in Examples, an excessively long washing treatment time results in deterioration of strength of the artificial blood vessel. Meanwhile, the above configuration makes it possible to produce an artificial blood vessel having greater strength.

In the step (4), temperature in the washing treatment is not limited to a particular one, and can be, for example, 4° C. or higher and 37° C. or lower, 4° C., or 37° C.

A time at which the step (4) is carried out is not limited to a particular one. Preferably, the step (4) is carried out after the step (3) (e.g., in the order of the step (1) the step (2)→the step (3)→the step (4), in the order of the step (1)→the step (3)→the step (2)→the step (4), or in the order of the step (1)→the step (3)→the step (4)→the step (2)). Of course, the present invention is not limited to the above-described timings. According to the configuration, it is possible to reliably remove at least both of "a destroyed substance(s) such as a cell(s) that occurs in the step (1)" and "DNase employed in the step (3)".

For example, in a case where the steps are carried out in the order of the step (1)→the step (2)→the step (3)→the step (4), it is possible to remove, by carrying out the step (4), "a destroyed substance(s) such as a cell(s) that occurs in the step (1)", "a peptide(s) which has not been adhered to the extracellular matrix and which has occurred in the step (2)" and "DNase employed in the step (3)".

Meanwhile, in a case where the steps are carried out in the order of the step (1)→the step (3)→the step (2)→the step (4), it is possible to remove, by carrying out the step (4), "a destroyed substance(s) such as a cell(s) that occurs in the step (1)", "a peptide(s) which has not been adhered to the extracellular matrix and which has occurred in the step (2)" and "DNase employed in the step (3)".

On the other hand, in a case where the steps are carried out in the order of the step (1)→the step (3)→the step (4)→the step (2), it is possible to remove "a destroyed substance(s) such as a cell(s) that occurs in the step (1)" and "DNase employed in the step (3)".

According to the method of the present embodiment for producing an artificial blood vessel, the step (4) can be carried out (e.g., in the order of the step (1)→the step (2)→the step (4), or in the order of the step (1)→the step (4)→the step (2)) even in a case where the step (3) is not carried out. Of course, the present invention is not limited to the above-described timings. According to the configuration, it is possible to reliably remove at least "a destroyed substance(s) such as a cell(s) that occurs in the step (1)".

For example, in a case where the steps are carried out in the order of the step (1)→the step (2)→the step (4), it is possible to remove, by carrying out the step (4), "a destroyed substance(s) such as a cell(s) that occurs in the step (1)" and "a peptide(s) which has not been adhered to the extracellular matrix and which has occurred in the step (2)".

Meanwhile, in a case where the steps are carried out in the order of the step (1)→the step (4)→the step (2), it is possible to remove, by carrying out the step (4), "a destroyed substance(s) such as a cell(s) that occurs in the step (1)".

In the above description, a concrete configuration of the step (4) is discussed. The step (4) is preferably a step that can more efficiently remove cells and cellular constituents (specifically, DNA) which remain in the extracellular matrix.

For example, on the premise that an amount of cells and cellular constituents which remain in the extracellular matrix obtained in the step (1) is 100 (100%), the step (4) is a step of reducing the amount to preferably 90 (90%) or less, further preferably 80 (80%) or less, further preferably 70 (70%) or less, further 60 (60%) or less, further preferably 50 (50%) or less, further preferably 40 (40%) or less, further preferably 30 (30%) or less, further preferably 20 (20%) or less, further preferably 10 (10%) or less, further preferably 5 (5%) or less, and further preferably 1 (1%) or less.

The method for producing the artificial blood vessel of the present invention can be configured as follows:

According to the method for producing the artificial blood vessel of the present invention, it is preferable that the n is an integer of 3 or more and 20 or less; and the m is an integer of 1 or more and 10 or less.

According to the method for producing the artificial blood vessel of the present invention, it is preferable that the X is a peptide linker made up of glycine whose number is or more, a peptide linker made up of alanine whose number is 1 or more, a peptide linker made up of serine whose number is 1 or more, or a peptide linker made up of at least two amino acids selected from the group consisting of glycine, alanine, and serine.

According to the method for producing the artificial blood vessel of the present invention, it is preferable that, in the step (1), the extracellular matrix is obtained by removing the cells by applying pressure to the bio-derived vascular tissue.

According to the method for producing the artificial blood vessel of the present invention, it is preferable that, in the step (1), the pressure to be applied is 200 MPa or higher and 1000 MPa or lower.

According to the method for producing the artificial blood vessel of the present invention, it is preferable that, in the step (2), a mixture of the extracellular matrix and the peptide is heated at 37° C. or higher and 100° C. or lower.

The method for producing the artificial blood vessel of the present invention preferably further includes the step of: (3) carrying out a DNase treatment with respect to the extracellular matrix.

The method for producing the artificial blood vessel of the present invention preferably further includes the step of: (4) washing the extracellular matrix with a cleaning liquid for a time period of three days or shorter.

According to the method for producing the artificial blood vessel of the present invention, it is preferable that the bio-derived vascular tissue is derived from a ratite, a bird, or a mammal.

Example

1. In Vitro Cell Adhesion Test

The following peptides were synthesized according to a known peptide synthesizing method. Note that "O" of the peptides represents hydroxyproline.

```
Peptide 1:   (POG)3GGG . . .       (SEQ ID NO: 6)

Peptide 2:   (POG)3GGGREDV . . .   (SEQ ID NO: 7)

Peptide 3:   (POG)7GGG . . .       (SEQ ID NO: 8)

Peptide 4:   (POG)7GGGREDV . . .   (SEQ ID NO: 9)

Peptide 5:   (OPG)7GGGREDV . . .   (SEQ ID NO: 10)
```

Then, an in vitro cell adhesion test was carried out on each of these peptides 1 through 5.

First, each of the peptides 1 through 5 was dissolved in a physiological saline solution to have an end concentration of 10 μM, so that five peptide-containing solutions were prepared.

Then, surfaces of cell culture dishes (adherent cell culture dishes manufactured by ASAHI GLASS CO., LTD.) were coated with the respective peptide-containing solutions. As a negative control, a culture dish was also prepared whose surface was coated with a physiological saline solution containing no peptide.

Then, a hundred thousand of human umbilical vein endothelial cells (HUVEC) were put in each of the culture dishes, and cultured at 37° C. under 5% $CO_2$ for 24 hours in an endothelial cell basal medium.

After the culture, the medium was removed from each of the culture dishes, and the surface of each of the culture dishes was washed with a physiological saline solution several times. The number of human umbilical vein endothelial cells was counted which still adhered to the surface of each of the culture dishes even after the washing. Then, calculated was a ratio of (i) the number of human umbilical vein endothelial cells which still adhered to the surface of each of the culture dishes even after the washing relative to (ii) the number of the human umbilical vein endothelial cells which were put in each of the culture dishes when the culture started.

FIG. 1 shows the result of the test. It was found that the peptide 4 of the peptides 1 through 5 had activity which caused the cells to adhere to the culture dish.

2. Production of Artificial Blood Vessel

An artificial blood vessel was produced with the use of the above peptide 4. The following description will discuss in detail a method for producing the artificial blood vessel.

First, a carotid artery (having a lumen whose cross sectional diameter was approximately 2.0 mm and a total length of approximately 40 cm) taken out of an ostrich's neck was washed with a physiological saline solution, and then packed in a physiological saline solution.

Then, the carotid artery which was being soaked in the physiological saline solution was pressurized at 1000 MPa for 10 minutes (with an ultra-high pressure processing apparatus manufactured by Kobe Steel, Ltd. (KOBELCO)). That is, with this pressurization, cells included in the carotid artery were destroyed and removed, and an extracellular matrix which constituted the carotid artery was extracted.

After the pressurization, the extracellular matrix derived from the carotid artery was left at 37° C. for three days in a physiological saline solution that contained 40 U/mL of DNase and 20 mM of $MgCl_2$. That is, this treatment completely decomposed cells and cellular constituents (specifically, DNA) which remained in the extracellular matrix.

After the extracellular matrix was treated with the DNase, the extracellular matrix was washed at 37° C. for three days in a physiological saline solution containing EDTA (ethylene diamine tetraacetic acid) whose concentration was 500 mg/L. That is, this treatment completely removed the cells, the cellular constituents, and the DNase from the extracellular matrix. Note that the extracellular matrix, which had been obtained from the carotid artery as above described, was stored at 4° C. in a state where the extracellular matrix was soaked in the physiological saline solution containing 500 mg/L of the EDTA.

Figure 2:
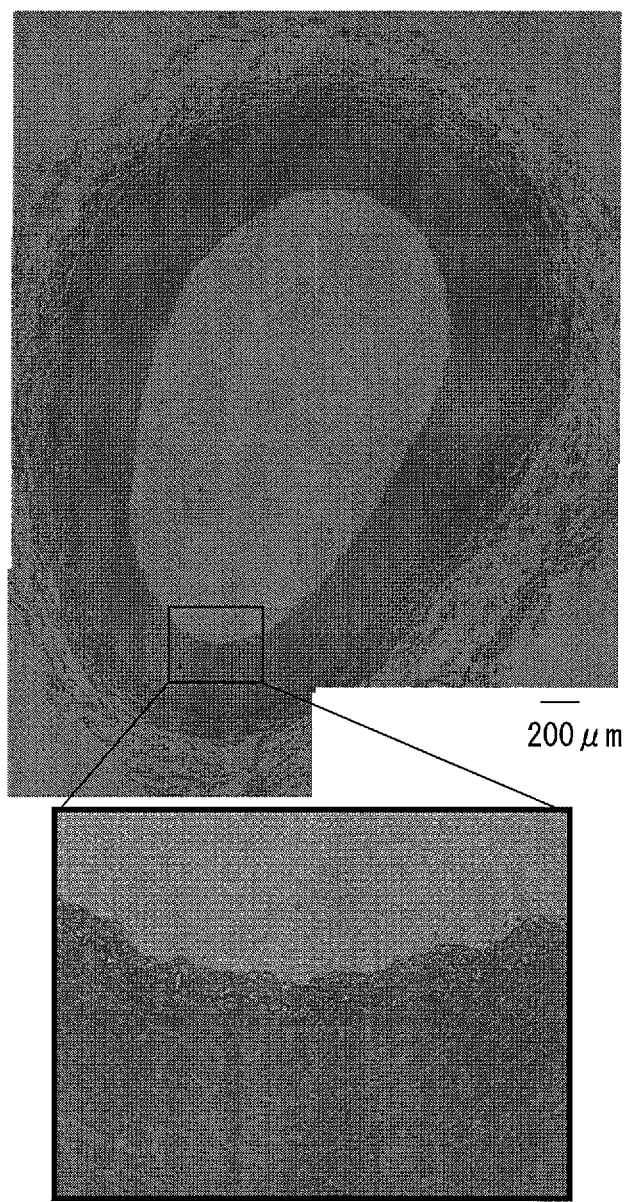
FIG. 2 is a photograph showing a chromatic figure of an extracellular matrix in Example of the present invention.

FIG. 2 shows the result of hematoxylin-eosine stain by which the washed extracellular matrix was stained. Note that the hematoxylin-eosine stain was carried out according to a known method.

As is clear from FIG. 2, no chromatic figure corresponding to a nucleus or cytoplasm (in other words, a cell) was observed in the washed extracellular matrix. That is, it was found that the cells and the cellular constituents were effectively removed from the washed extracellular matrix.

Next, components contained in the washed extracellular matrix were specified by a known staining method. Specifically, it was checked whether or not the washed extracellular matrix contained von Willebrand factor (vWF), Vimentin, α Smooth muscle actin (αSMA), and a substance stained by Elastica van Gieson stain (EVG).

Note that whether or not the washed extracellular matrix contained the von Willebrand factor (vWF) was checked with an anti-human VIII-Factor related antigen and a rabbit polyclonal antibody manufactured by Dako. As a specific staining method, a generally known immunostaining method was employed.

Whether or not the washed extracellular matrix contained the Vimentin was checked with Monoclonal Mouse Anti-VIM V9 manufactured by Dako. As a specific staining method, a generally known immunostaining method was employed.

Whether or not the washed extracellular matrix contained the α Smooth muscle actin (αSMA) was checked with anti-human smooth muscle actin and 1A4 mouse monoclonal antibody manufactured by Dako. As a specific staining method, a generally known immunostaining method was employed.

The Elastica van Gieson stain was carried out according to a generally known staining method.

Figure 3:
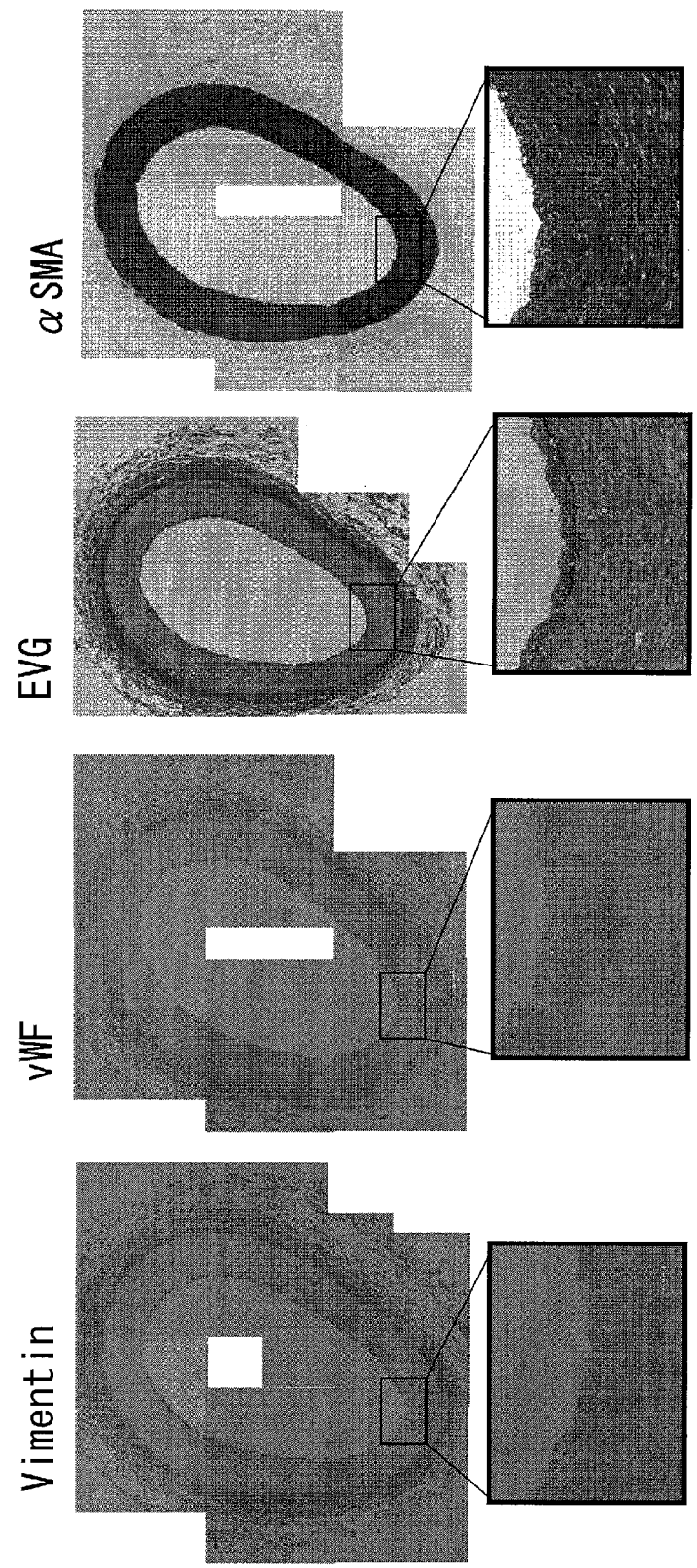
FIG. 3 is a photograph showing chromatic figures of respective extracellular matrices in Example of the present invention.

FIG. 3 shows above staining results. As is clear from FIG. 3, the washed extracellular matrix contained all of the von Willebrand factor (vWF), the Vimentin, the α Smooth muscle actin (αAMA), and the substance stained by the Elastica van Gieson stain each of which was being in a state close to an intact state.

Lastly, the extracellular matrix derived from the carotid artery, which matrix had been obtained as above described, was (i) soaked in a physiological saline solution containing the peptide 4 with a concentration of 10 μM, (ii) heated at 60° C. for 60 minutes, and then (iii) gradually cooled at room temperature. That is, through these treatments, the peptide 4 was adhered to a surface of the lumen of the extracellular matrix. The extracellular matrix to which the peptide 4 has been adhered is hereinafter referred to as "artificial blood vessel of the present Example".

Figure 4:
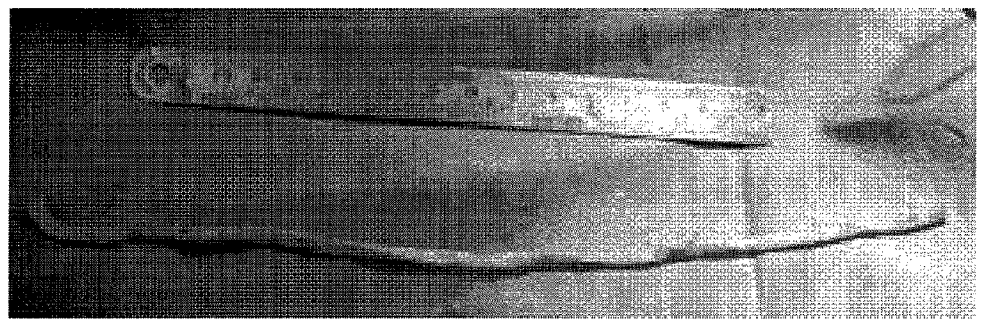
FIG. 4 is a photograph showing an artificial blood vessel in Example of the present invention.

FIG. 4 shows a photograph of the artificial blood vessel of the present Example. The artificial blood vessel of the present Example had an inner diameter of approximately 2.0 mm and the total length of approximately 40 cm. This size of the artificial blood vessel of the present Example was substantially equal to that of the carotid artery taken out of the ostrich's neck.

3. Transplantation of Artificial Blood Vessel, and Observation of Transplanted Artificial Blood Vessel The artificial blood vessel of the present Example was transplanted into a pig, and then functions of the transplanted artificial blood vessel were tested.

The artificial blood vessel of the present Example was transplanted into the pig through a typical Femoral-Femoral crossover bypass surgery. The following description will briefly summarize the transplantation surgery of the artificial blood vessel with reference to FIG. 5.

Figure 5:
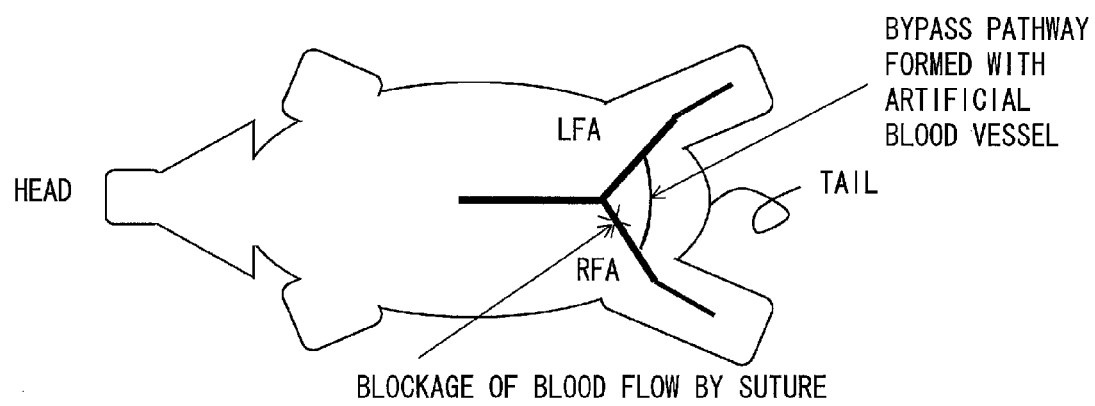
FIG. 5 is a view for explaining an overview of surgery for transplanting an artificial blood vessel with the use of Femoral-Femoral crossover bypass in Example of the present invention.

As shown in FIG. 5, first, a femoral artery of a right leg side (RFA) was sutured to be closed. This blocked a blood flow from a sutured part toward a toe side.

Simultaneously, a bypass pathway from a femoral artery of a left leg side (LFA) to the femoral artery of the right leg side was formed with the use of the above artificial blood vessel. The bypass pathway thus formed restored the blood flow from the sutured part toward the toe side.

Breeding of the pig on which the transplantation surgery had been performed was continued in a state where a surgical part of the pig was saturated, and postoperative progress of the pig was observed. The following description will discuss (i) the postoperative progress of the pig into which the artificial blood vessel had been transplanted and (ii) the result of the observation of the transplanted artificial blood vessel.

<3-1. Test Result 1>

A state of walking of the pig, on which the transplantation had been performed, was observed. If a thrombus is formed in the artificial blood vessel of the present Example which was used as the bypass pathway, the blood flow toward the right leg side is blocked, so that the pig gets difficulty in walking. On the other hand, if no thrombus is formed in the artificial blood vessel of the present Example which was used as the bypass pathway, the blood flow toward the right leg side is maintained, so that the pig can normally walk. That is, by observing the state of walking of the pig, it is possible to determine whether or not a thrombus has been formed in the artificial blood vessel.

As a result of observing the state of walking of the pig on which the transplantation surgery had been performed, the pig kept normally walking even when two weeks elapsed after the surgery. That is, even when two weeks elapsed after the surgery, no thrombus was formed in the artificial blood vessel, and the blood flow toward the right leg side was normally maintained.

<3-2. Test Result 2>

With the use of a known laser Doppler, it was checked whether or not a blood flow existed in a center region of the artificial blood vessel, forming the bypass pathway, of the pig on the 21st day after the surgery. (a) and (b) of FIG. 6 show the test result.

Figure 6:
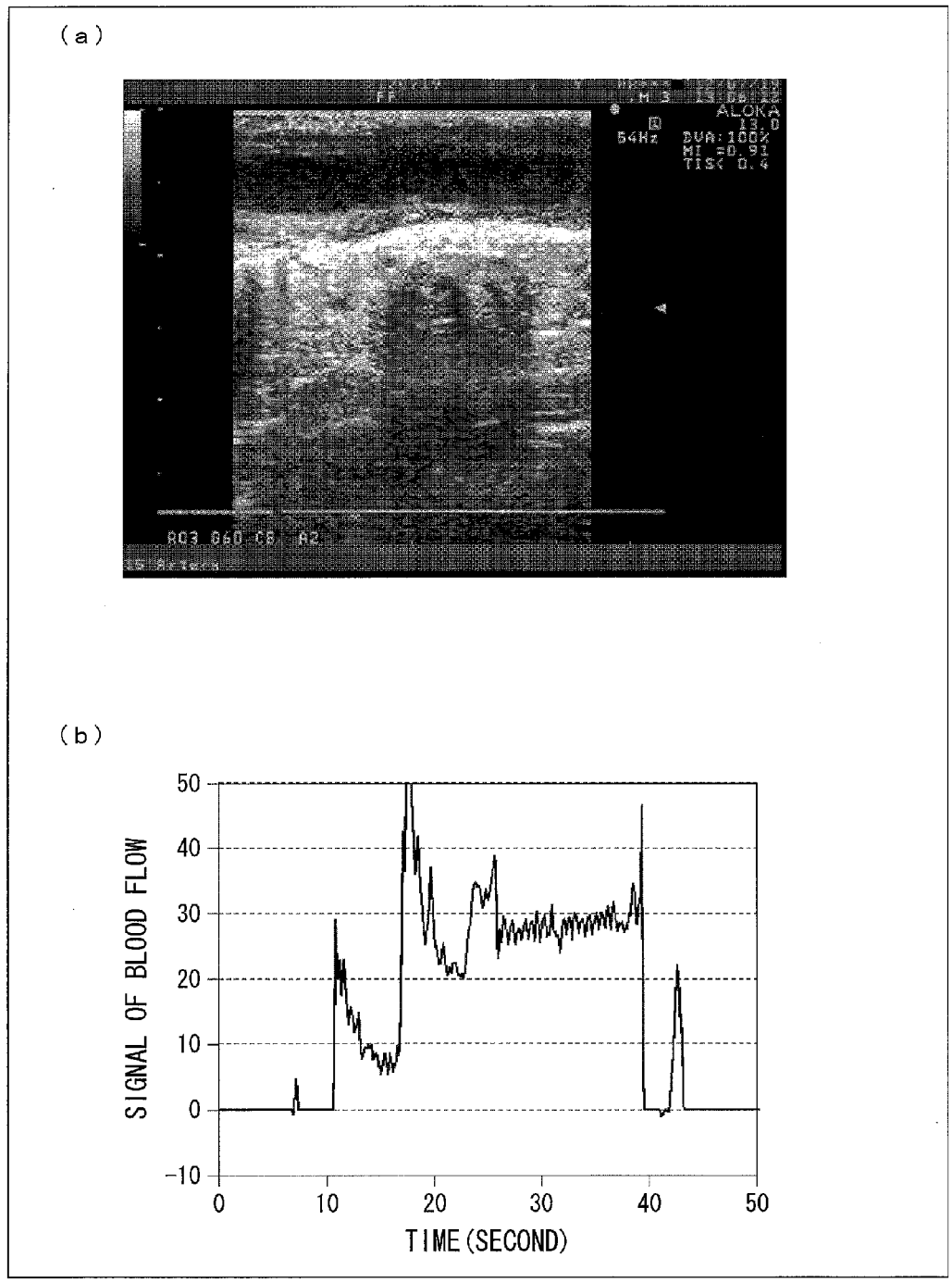
FIG. 6 is a graph illustrating, in (a) and (b), a result of confirming, with the use of a laser Doppler, whether or not a blood flow exists in a region of an artificial blood vessel forming a bypass pathway, in Example of the present invention.

(a) of FIG. 6 is an image showing the result of an ultrasonic diagnosis of the center region of the artificial blood vessel forming the bypass pathway. (b) of FIG. 6 shows a signal of the blood flow in the center region of the artificial blood vessel forming the bypass pathway.

As shown in (a) and (b) of FIG. 6, a normal blood flow was found in the artificial blood vessel even when 21 days elapsed after the surgery. That is, even when 21 days elapsed after the surgery, no thrombus was formed in the artificial blood vessel, and the normal blood flow toward the right leg side was maintained.

It was also found that blood pressure of the center region of the artificial blood vessel forming the bypass pathway was 60/49 which was substantially equal to blood pressure (79/54) of the femoral artery of the left leg side. This demonstrated that the artificial blood vessel secured a sufficient amount of blood flow.

<3-3. Test Result 3>

On the 20th day after the surgery, the transplanted part of the pig was opened, and whether or not a blood flow existed in the transplanted artificial blood vessel was observed by the naked eyes. Note that, in (a) and (b) of FIG. 7, "RFA" represents a part of the artificial blood vessel on a side closer to the femoral artery of the right leg side, and "LFA" represents a part of the artificial blood vessel on a side closer to the femoral artery of the left leg side.

Figure 7:
FIG. 7 is a photograph showing, in (a) and (b), an artificial blood vessel in Example of the present invention.
Figure 7:
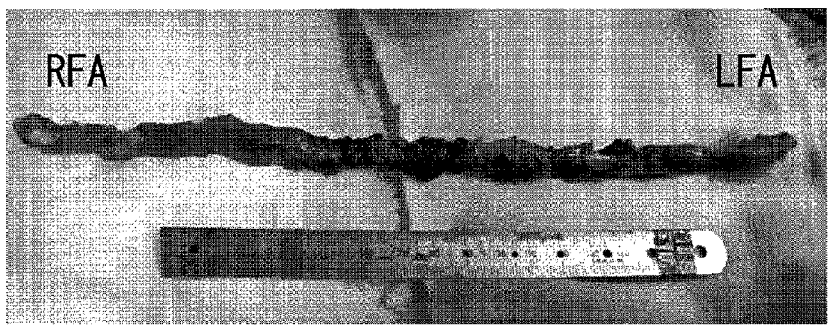
Figure 7:
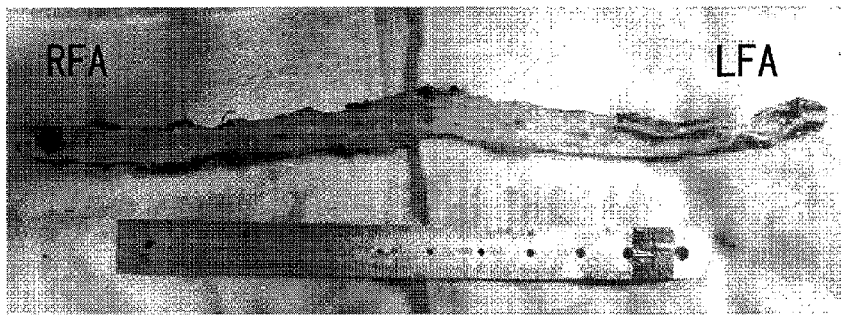

(a) of FIG. 7 shows a state where the transplanted part of the pig was opened on the 20th day after the surgery. As shown in (a) of FIG. 7, pulsation of the transplanted artificial blood vessel was confirmed in both (i) the part closer to the femoral artery of the right leg side and (ii) the part closer to the femoral artery of the left leg side. This demonstrates that a sufficient amount of blood flew to the femoral artery of the right leg side via the bypass pathway formed with the artificial blood vessel.

(b) of FIG. 7 shows a state of the artificial blood vessel taken out of the pig on the 20th day after the surgery. The upper photograph of (b) of FIG. 7 shows a state of the artificial blood vessel which has not been cut open. The lower photograph of (b) of FIG. 7 shows a state of the artificial blood vessel which has been cut open.

As shown in (b) of FIG. 7, the transplanted artificial blood vessel was in a normal form. This demonstrates that blood normally flew through the transplanted artificial blood vessel. As is clear from (b) of FIG. 7, no thrombus was found in the transplanted artificial blood vessel.

Figure 8:
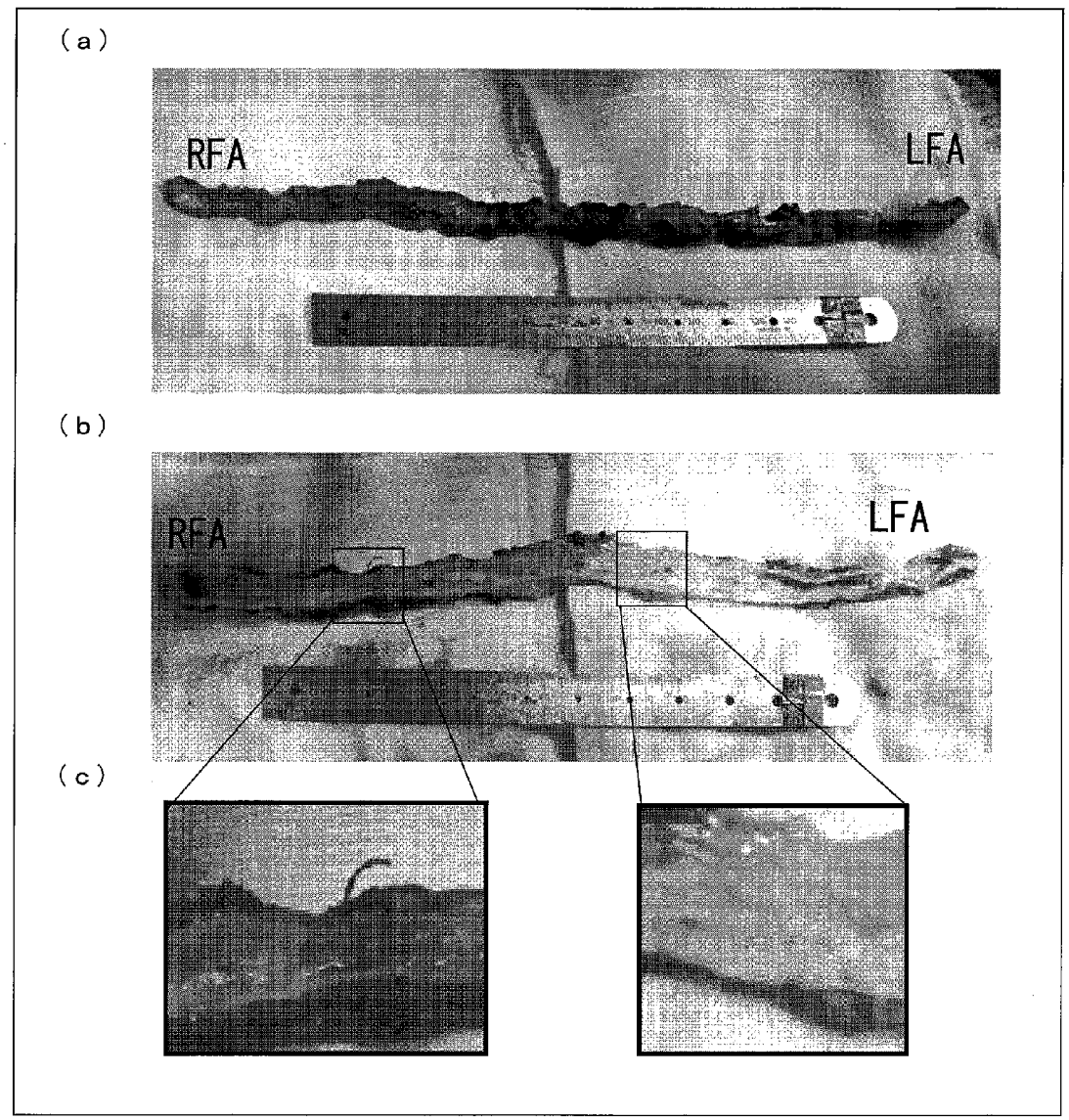
FIG. 8 is a photograph showing, in (a) through (c), a state of an artificial blood vessel to which a peptide had been added and which was transplanted 20 days ago, in Example of the present invention.
Figure 9:
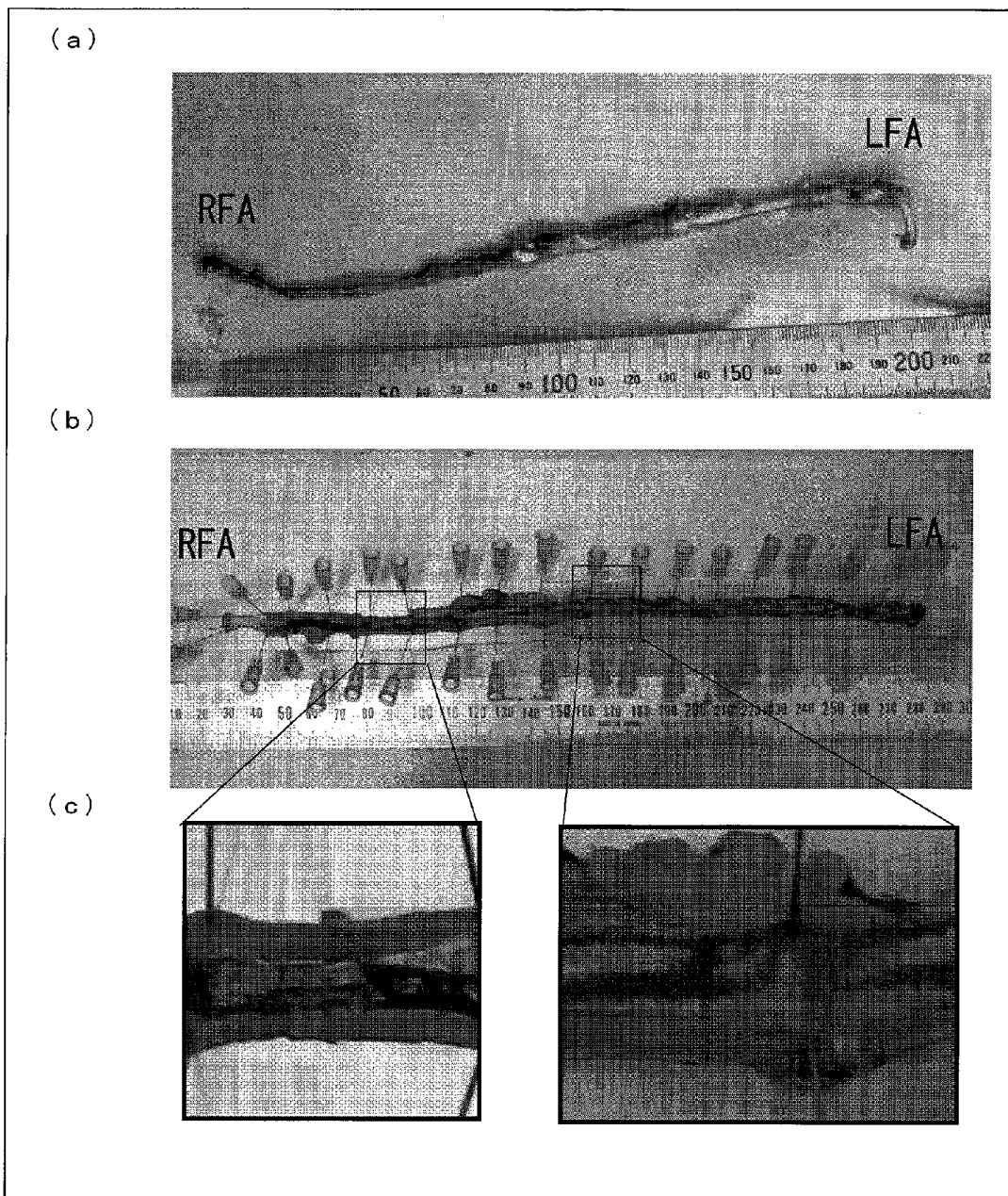
FIG. 9 is a photograph showing, in (a) through (c), a state of an artificial blood vessel to which a peptide had not been added and which was transplanted 7 days ago, in Example of the present invention.

FIG. 8 and FIG. 9 show further detailed states of transplanted artificial blood vessels. FIG. 8 shows a result obtained by observing a state of the artificial blood vessel, to which the peptide had been added, of the present Example taken out of the pig on the 20th day after the surgery. FIG. 9 shows a result obtained by observing a state of an artificial blood vessel (negative control) to which no peptide had been added and which was taken out of a pig on the 7th day after the artificial blood vessel was transplanted into the pig.

As shown in FIG. 8, the transplanted artificial blood vessel of the present Example to which the peptide had been added was in a normal form. This demonstrates that a normal blood flow existed in the transplanted artificial blood vessel.

Further, no thrombus was found in the artificial blood vessel which was cut open.

On the other hand, as shown in FIG. 9, the transplanted artificial blood vessel (negative control) to which no peptide had been added was in an abnormal form. This demonstrates that a normal blood flow did not exist in the transplanted artificial blood vessel. That is, this demonstrates that (i) a thrombus was formed in the artificial blood vessel (negative control) to which no peptide had been added and (ii) the thrombus blocked a blood flow toward a femoral artery of a right leg side.

Further, the thrombus was found in the artificial blood vessel which was cut open.

<3-4. Test Result 4>

On the 20th day after the surgery, the transplanted part of the pig was opened, and whether or not a blood flow existed in the transplanted artificial blood vessel was observed by the naked eyes. In addition, an inner part of the artificial blood vessel was observed with an endoscope so as to confirm whether or not a thrombus had been formed.

Figure 10:
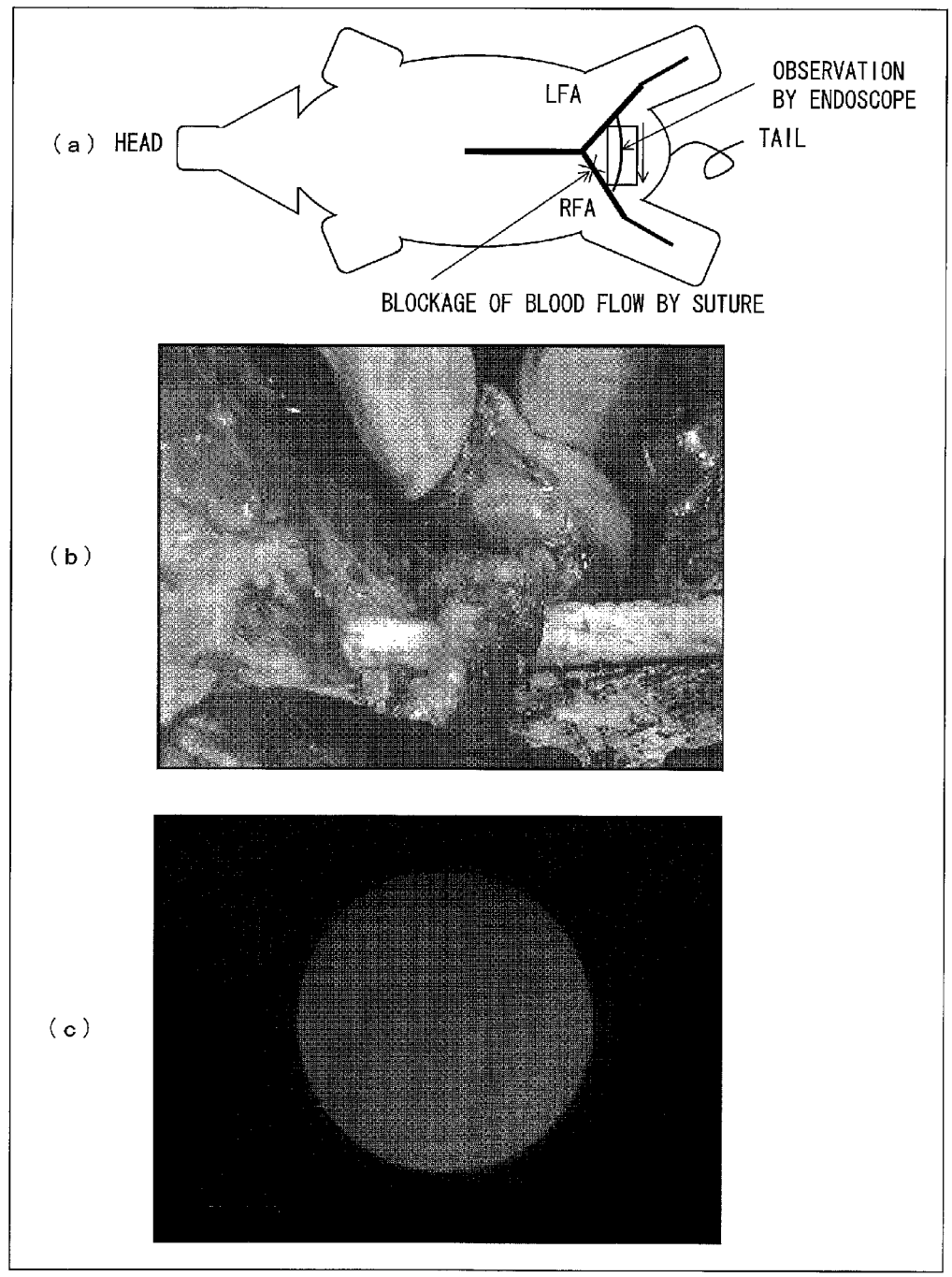
FIG. 10 is a view illustrating, in (a) through (c), a state of an artificial blood vessel which has been transplanted, in Example of the present invention.

(b) of FIG. 10 shows a state where the transplanted part of the pig was opened on the 20th day after the surgery. As shown in (b) of FIG. 10, pulsation was confirmed in the artificial blood vessel transplanted into the pig. This demonstrates that the sufficient amount of blood flew toward the femoral artery of the right leg side via the bypass pathway formed with the artificial blood vessel.

(c) of FIG. 10 shows a result obtained by observing with the endoscope the inner part of the artificial blood vessel shown in (b) of FIG. 10. Note that, as shown in (a) of FIG. 10, a state of the inner part of the artificial blood vessel was sequentially observed from the femoral artery of the left leg side (LFA) to the femoral artery of the right leg side (RFA) in this test. (c) of FIG. 10 shows an example photograph of a plurality of sequentially taken photographs.

As shown in the example photograph of (c) of FIG. 10, no thrombus was formed in the artificial blood vessel.

<3-5. Test Result 5>

The form of the artificial blood vessel on the 20th day after the surgery was observed by intravascular ultrasound imaging (IVAS). (a) and (b) of FIG. 11 show results of the intravascular ultrasound imaging.

Figure 11:
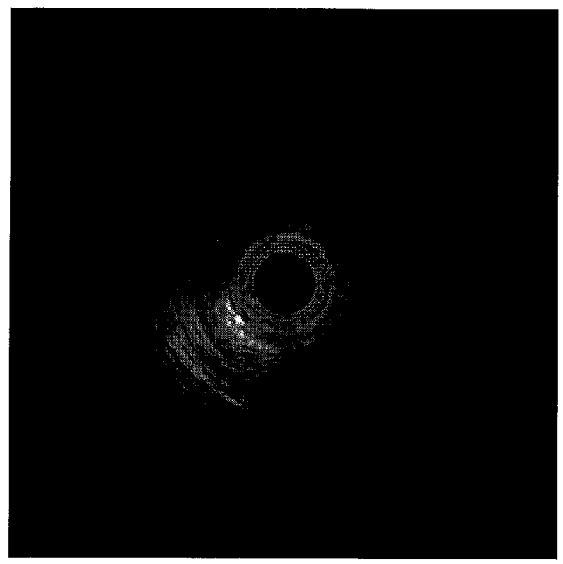
FIG. 11 is a view illustrating, in (a) and (b), a result of intravascular ultrasound imaging carried out with respect to an artificial blood vessel which has been transplanted, in Example of the present invention.
Figure 11:
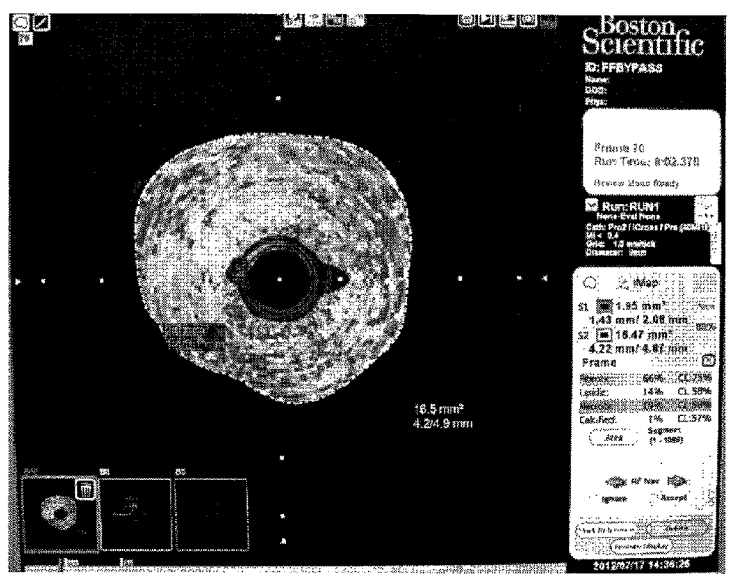

It was found from (a) and (b) of FIG. 11 that the transplanted artificial blood vessel had (i) a lumen whose size was approximately 1.5 mm and (ii) an exterior covered with a fiber tissue. Neither a state where a lipid was accumulated in the artificial blood vessel nor a state where the artificial blood vessel was calcified was observed from (a) and (b) of FIG. 11.

The artificial blood vessel was taken out of the pig on the 20th day after the surgery, and a state of the artificial blood vessel was observed in more detail. Specifically, the artificial blood vessel was stained by hematoxylin-eosine stain and von Willebrand stain so as to confirm bio-derived cells existing inside and outside of the artificial blood vessel on the 20th day after the transplantation. Note that the hematoxylin-eosine stain and the von Willebrand stain were specifically carried out according to known methods.

Figure 12:
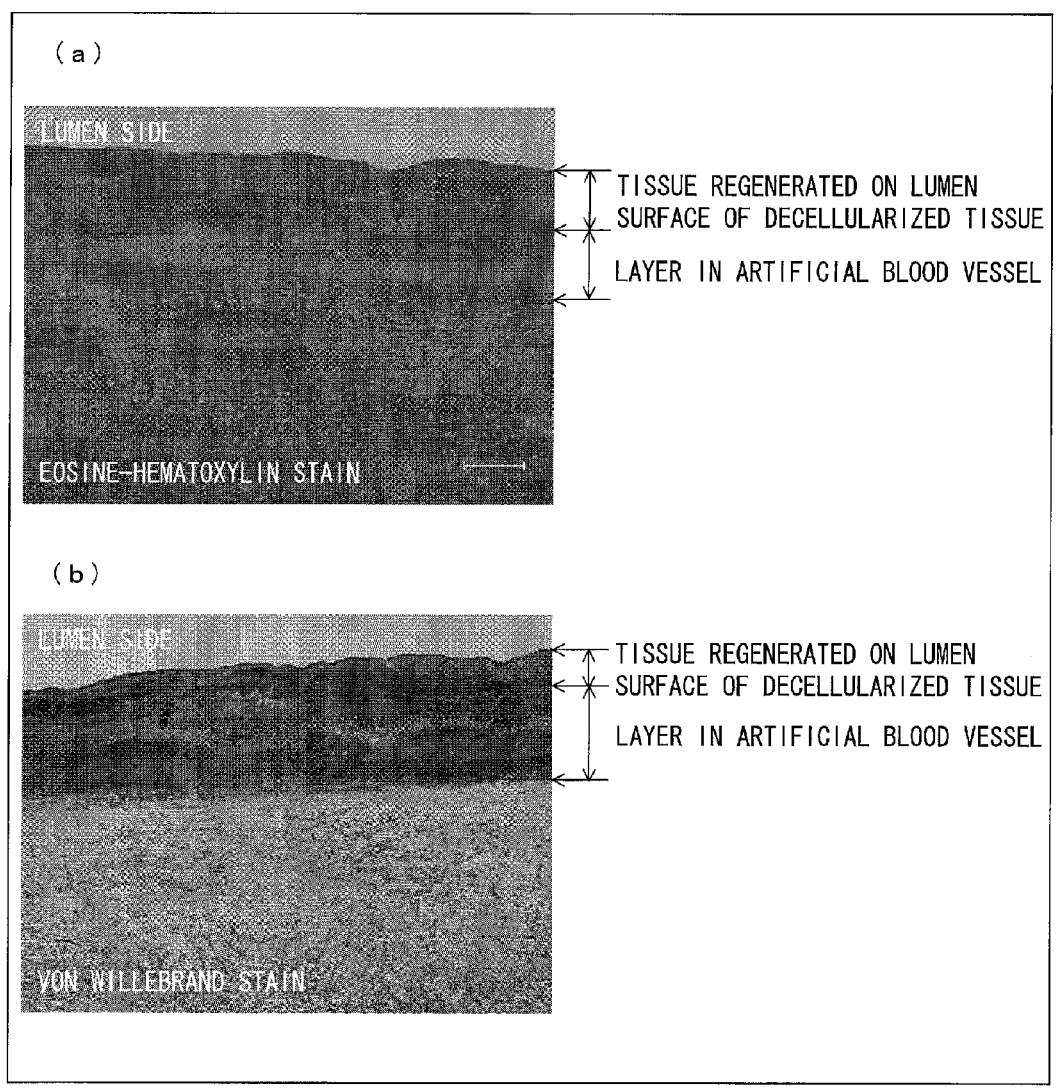
FIG. 12 is a photograph showing, in (a) and (b), a result of staining an artificial blood vessel, which has been transplanted in Example of the present invention, with a hematoxylin-eosine stain and a von Willebrand stain.

(a) of FIG. 12 shows a result of the hematoxylin-eosine stain. (b) of FIG. 12 shows a result of the von Willebrand stain.

As shown in (a) of FIG. 12, many infiltrated cells were observed inside the artificial blood vessel, and regeneration of a thick tissue was observed on a surface of the lumen of the artificial blood vessel.

Further, as is clear from (b) of FIG. 12, (i) the cells which infiltrated inside the artificial blood vessel and (ii) cells included in the tissue regenerated on the surface of the lumen of the artificial blood vessel, which were observed in (a) of FIG. 12, reacted positively to the von Willebrand stain. This demonstrated that these cells were endothelial cells.

<3-6. Test Result 6>

Influence was confirmed which was exerted on strength of an artificial blood vessel by a washing time period when the artificial blood vessel was produced.

Specifically, strength of artificial blood vessels was tested, which had been prepared through the procedures in above <2. Production of artificial blood vessel> with different time periods (i.e., 3 days or 11 days) for washing the extracellular matrix with a physiological saline solution containing EDTA (whose concentration was 500 mg/L) after the DNase treatment (i.e., three-day DNase treatment).

Figure 13:
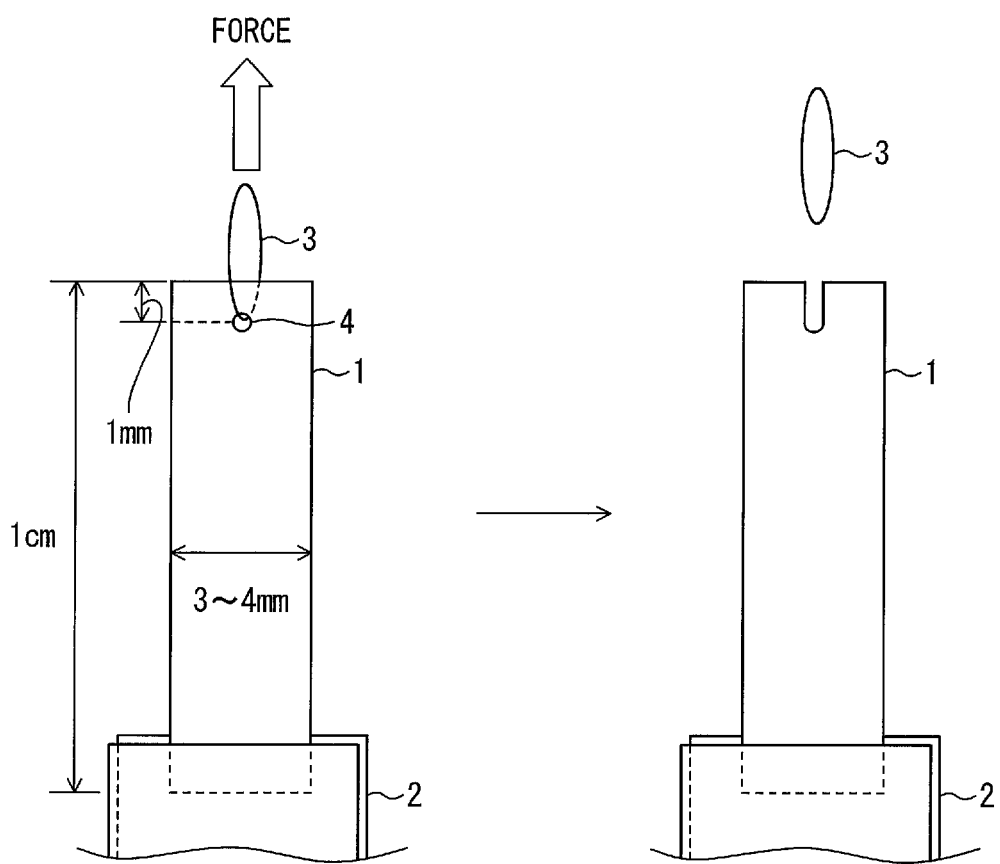
FIG. 13 is a view for explaining a method for testing strength of an artificial blood vessel in Example of the present invention.

First, a testing method is described with reference to FIG. 13.

A hole 4 was formed in the vicinity of one end part of an artificial blood vessel 1 which was approximately 1 cm in length and approximately 3 to 4 mm in width. A string 3 was passed through the hole 4. Note that the hole 4 was formed at a location distant by 1 mm from the end part. The other end part of the artificial blood vessel 1 was fixed to a clamp 2.

The string 3 was pulled at a pulling rate of 2 mm/min. Then, force was measured which was applied to the string 3 to break the artificial blood vessel 1 and to cause the string 3 to come off from the artificial blood vessel 1. From the measurement result, it is possible to predict the strength of the artificial blood vessel (specifically, strength against blood pressure, strength against a suturing treatment during surgery, etc.)

Figure 14:
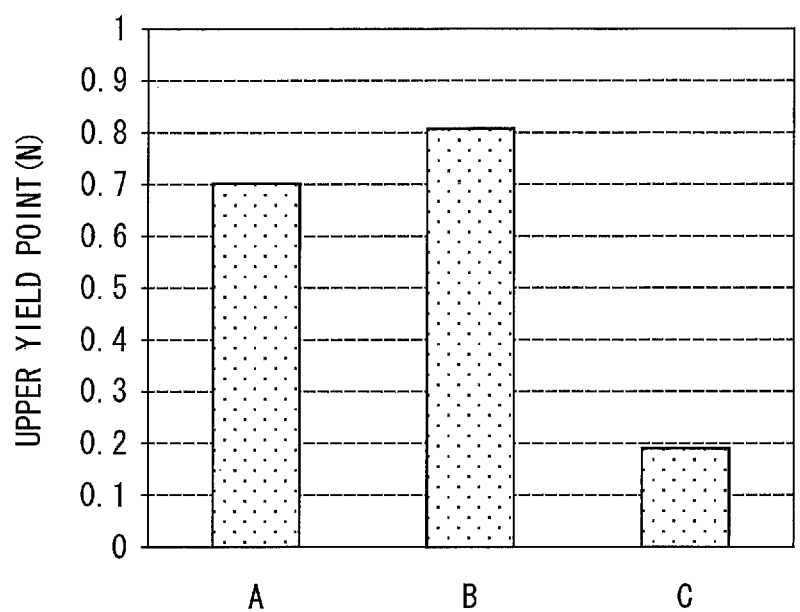
FIG. 14 is a graph illustrating strength of an artificial blood vessel in Example of the present invention.

FIG. 14 shows test results. In FIG. 14, "A" shows the test result of a native carotid artery (i.e., untreated carotid artery) taken out of an ostrich's neck, "B" shows the test result of an artificial blood vessel which was subjected to a three-day DNase treatment and then washed for three days, and "C" shows the test result of an artificial blood vessel which was subjected to a three-day DNase treatment and then washed for 11 days.

As is clear from FIG. 14, an excessively long washing time period deteriorated the strength of the artificial blood vessel.

<3-7. Test Result 7>

In this test, cell removing effects of the steps (1), (3) and (4) described in <2. Production of artificial blood vessel> were checked. Note that, in this test, a rat-derived vascular tissue (descending aorta) and an ostrich-derived vascular tissue (carotid artery) were used to produce artificial blood vessels.

Note also that, in this test, the artificial blood vessels were stained by hematoxylin-eosine stain in each of the steps for producing the artificial blood vessels in order to confirm cells (cell nuclei) remaining in an extracellular matrix.

Figure 15:
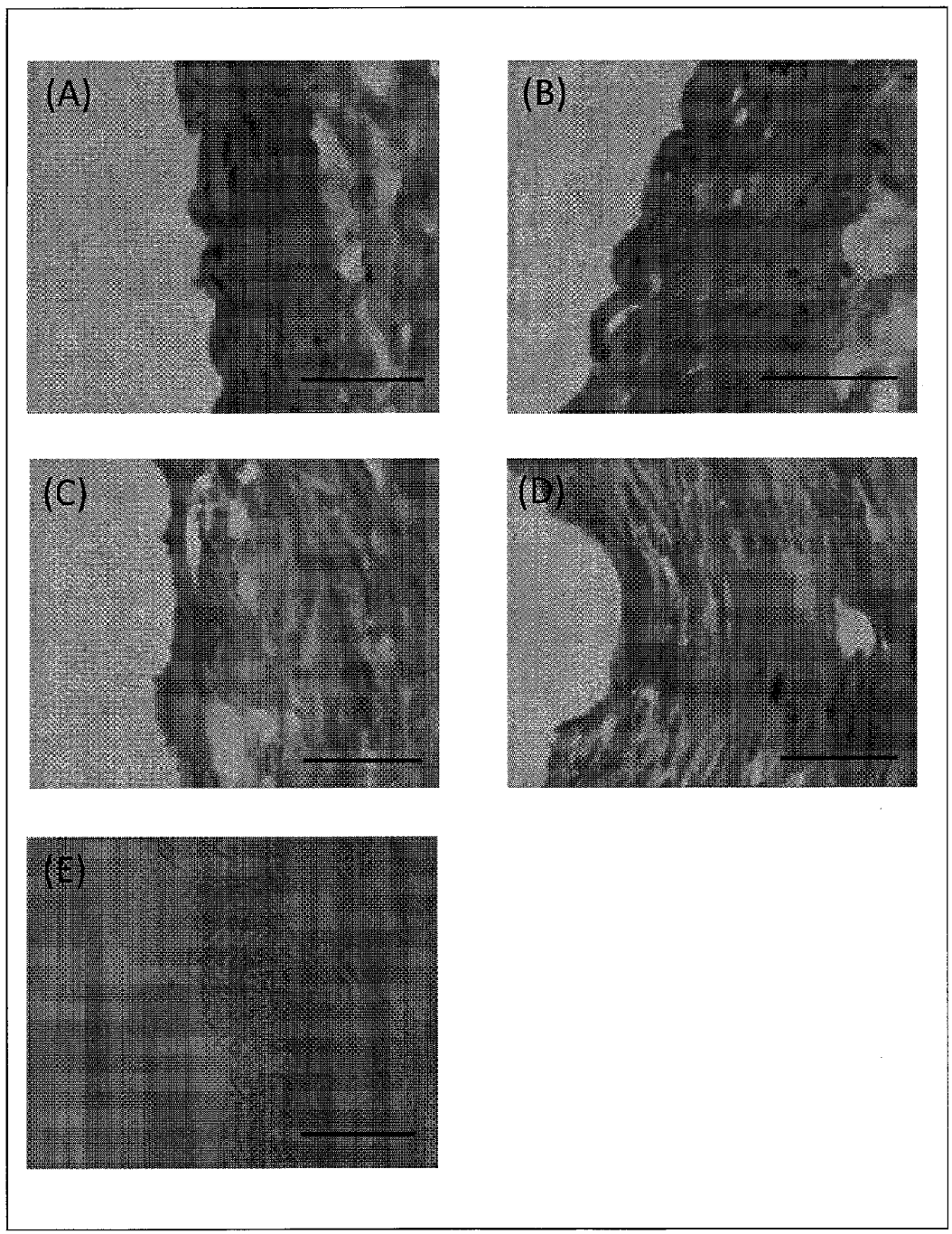
FIG. 15 is a photograph showing, in (A) through (E), effects of removing cells in the steps (1), (3), and (4) in Example of the present invention.

(A) of FIG. 15 shows a chromatic figure of the descending aorta of the rat before the step (1) is carried out (i.e., before a high pressure treatment). (B) of FIG. 15 shows a chromatic figure of the descending aorta of the rat after the step (1) is carried out (i.e., after the high pressure treatment). (C) of FIG. 15 shows a chromatic figure of the carotid artery of the ostrich before the step (1) is carried out (i.e., before a high pressure treatment). (D) of FIG. 15 shows a chromatic figure of the carotid artery of the ostrich after the step (1) is carried out (i.e., after the high pressure treatment). (E) of FIG. 15 shows a chromatic figure of the carotid artery of the ostrich after the step (3) (i.e., three-day DNase treatment) and the step (4) (i.e., three-day washing treatment) are carried out.

As is clear from (A) through (E) of FIG. 15, as the steps proceeded like (1), (3), and (4), the number of cells (cell nuclei) remaining in the extracellular matrix decreased. Particularly, the steps (3) and (4) brought about excellent cell removing effects.

The present invention is not limited to the description of the above configuration, and can therefore be modified by a skilled person in the art within the scope of the claims. Namely, an embodiment or example derived from a proper combination of technical means disclosed in different embodiments or examples is encompassed in the technical scope of the present invention.

INDUSTRIAL APPLICABILITY

The present invention is applicable to an artificial blood vessel transplantable into a living body etc. An artificial blood vessel of the present invention can be used as (i) an artificial blood vessel for an artery and (ii) an artificial blood vessel for a vein. The artificial blood vessel of the present invention can also be used as (i) an artificial blood vessel to be transplanted into an organism whose species is different from that of an organism from which an extracellular matrix is derived and (ii) an artificial blood vessel to be transplanted into an organism whose species is identical with that of an organism from which an extracellular matrix is derived.

REFERENCE SIGNS LIST

1: Artificial blood vessel
2: Clamp
3: String
4: Hole

The invention claimed is:

1. An artificial blood vessel formed from an extracellular matrix obtained by removing cells from a bio-derived vascular tissue, wherein:
   a cross sectional diameter of a lumen of said artificial blood vessel is 4 mm or less; and
   a peptide has been added to the extracellular matrix, the peptide including an amino acid sequence $(POG)_n$-X-$(REDV)_m$ wherein n is an integer of 3 or more and 50 or less, and m is an integer of 1 or more and 50 or less, and X is a peptide linker made up of glycine whose number is 2 or more, a peptide linker made up of alanine whose number is 1 or more, a peptide linker made up of serine whose number is 1 or more, or a peptide linker made up of alanine and serine.

2. The artificial blood vessel as set forth in claim 1, wherein:
   the n is an integer of 3 or more and 20 or less; and
   the m is an integer of 1 or more and 10 or less.

3. The artificial blood vessel as set forth in claim 1, wherein:
   the extracellular matrix is obtained by removing cells by applying pressure to the bio-derived vascular tissue.

4. The artificial blood vessel as set forth in claim 1, wherein the extracellular matrix has been subjected to a DNase treatment.

5. The artificial blood vessel as set forth in claim 1, wherein:
   the extracellular matrix has been washed with a cleaning liquid for a time period of three days or shorter.

6. The artificial blood vessel as set forth in claim 1, wherein:
   the extracellular matrix contains a von Willebrand factor, Vimentin, α Smooth muscle actin, a substance stained by an Elastica van Gieson stain, collagen, and elastin which are maintained in an intact state.

7. The artificial blood vessel as set forth in claim 1 wherein:
   the bio-derived vascular tissue is derived from a ratite, a bird, or a mammal.

8. A method for producing an artificial blood vessel, said method comprising the steps of:
   (1) obtaining an extracellular matrix by removing cells from a bio-derived vascular tissue whose lumen has a cross sectional diameter of 4 mm or less; and
   (2) adding, to the extracellular matrix, a peptide that includes an amino acid sequence $(POG)_n$-X-$(REDV)_m$ wherein n is an integer of 3 or more and 50 or less, and m is an integer of 1 or more and 50 or less, and X is a peptide linker made up of glycine whose number is 2 or more, a peptide linker made up of alanine whose number is 1 or more, a peptide linker made up of serine whose number is 1 or more, or a peptide linker made up of alanine and serine.

9. The method as set forth in claim 8, wherein:
   the n is an integer of 3 or more and 20 or less; and
   the m is an integer of 1 or more and 10 or less.

10. The method as set forth in claim 8, wherein:
    in the step (1), the extracellular matrix is obtained by removing the cells by applying pressure to the bio-derived vascular tissue.

11. The method as set forth in claim 10, wherein:
    in the step (1), the pressure to be applied is 200 MPa or higher and 1000 MPa or lower.

12. The method as set forth in claim 8, wherein:
in the step (2), a mixture of the extracellular matrix and the peptide is heated at 37° C. or higher and 100° C. or lower.

13. The method as set forth in claim 8, further comprising the step of:
(3) carrying out a DNase treatment with respect to the extracellular matrix.

14. The method as set forth in claim 8, further comprising the step of:
(4) washing the extracellular matrix with a cleaning liquid for a time period of three days or shorter.

15. The method as set forth in claim 8, wherein:
the bio-derived vascular tissue is derived from a ratite, a bird, or a mammal.

* * * * *